United States Patent
Hammen

(10) Patent No.: US 6,251,278 B1
(45) Date of Patent: *Jun. 26, 2001

(54) PROCESS FOR SEPARATING A SUBSTANCE FROM A MIXTURE

(75) Inventor: Richard Frederick Hammen, Missoula, MT (US)

(73) Assignee: ChromatoChem, Inc., Missoula, MT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,450

(22) Filed: Mar. 3, 1999

Related U.S. Application Data

(63) Continuation of application No. 08/949,448, filed on Oct. 14, 1997, now abandoned, which is a continuation of application No. 08/714,523, filed on Sep. 16, 1996, now abandoned, which is a continuation of application No. 08/397,414, filed on Mar. 1, 1995, now abandoned, which is a continuation of application No. 08/070,554, filed on Jun. 1, 1993, now abandoned, which is a division of application No. 07/682,393, filed on Apr. 2, 1991, now Pat. No. 5,240,602, which is a continuation of application No. 07/485,866, filed on Feb. 23, 1990, now abandoned, which is a continuation of application No. 07/187,765, filed on Apr. 29, 1988, now abandoned, which is a continuation-in-part of application No. 07/058,988, filed on Jun. 8, 1987, now abandoned.

(51) Int. Cl.$^7$ .................................................. B01D 15/08
(52) U.S. Cl. .................. 210/635; 210/656; 210/198.2; 210/502.1
(58) Field of Search ................... 210/635, 656, 210/198.2, 502.1; 502/401, 402; 530/413, 417; 435/180, 181

(56) References Cited

U.S. PATENT DOCUMENTS

| | | | |
|---|---|---|---|
| 3,715,278 | * 2/1973 | Miller | 195/63 |
| 3,846,306 | * 11/1974 | Barker | 210/198.2 |
| 3,888,864 | * 6/1975 | Cleeland | 260/285 |
| 4,007,089 | * 2/1977 | Smith | 195/68 |
| 4,029,583 | * 6/1977 | Ho Chang | 210/198.2 |
| 4,071,409 | * 1/1978 | Messing | 435/176 |
| 4,132,596 | * 1/1979 | Meiller | 195/63 |
| 4,163,001 | * 7/1979 | Carumpalos | 106/20 R |
| 4,177,038 | * 12/1979 | Biebricher | 210/198.2 |
| 4,199,330 | * 4/1980 | Nestrick | 55/67 |
| 4,210,722 | * 7/1980 | Silver | 435/176 |
| 4,257,938 | * 3/1981 | Hosoi | 210/656 |
| 4,330,440 | * 5/1982 | Ayers | 210/635 |
| 4,352,884 | * 10/1982 | Nakashima | 435/180 |
| 4,406,792 | * 9/1983 | Glad | 210/656 |
| 4,415,663 | * 11/1983 | Symon | 435/176 |
| 4,415,665 | * 11/1983 | Mosbach | 435/179 |
| 4,431,544 | * 2/1984 | Atkinson | 210/635 |
| 4,438,196 | * 3/1984 | Lantero | 435/96 |
| 4,451,568 | * 5/1984 | Schneider | 435/181 |
| 4,532,232 | * 7/1985 | Larsson | 502/403 |
| 4,540,486 | * 9/1985 | Ramsden | 210/198.2 |
| 4,581,337 | * 4/1986 | Frey | 436/533 |
| 4,610,962 | * 9/1986 | Takagi | 435/179 |

OTHER PUBLICATIONS

Snyder, Introduction to Modern Liquid Chromatography John Wiley & Sons, Inc., New York, 1979, pp. 126, 127, and 272–275.*

Merck Index, Tenth Edition, 1983, Published by Merck & Co., Inc., Rahway, New Jersey p. 1092.*

* cited by examiner

Primary Examiner—Ernest G. Therkorn
(74) Attorney, Agent, or Firm—Richard F. Trecartin; Flehr Hohbach Test Albritton & Herbert LLP

(57) ABSTRACT

Chromatographic material having the general formula S-B-X-Y-L where S is a solid support, B is a binding group, X is a substantially non-ionic hydrophilic organic spacer, Y is a coupling group and L is an affinity ligand. The chromatographic material is substantially free of non-specific adsorption and is stable at high pH.

6 Claims, 11 Drawing Sheets

FIG.—6

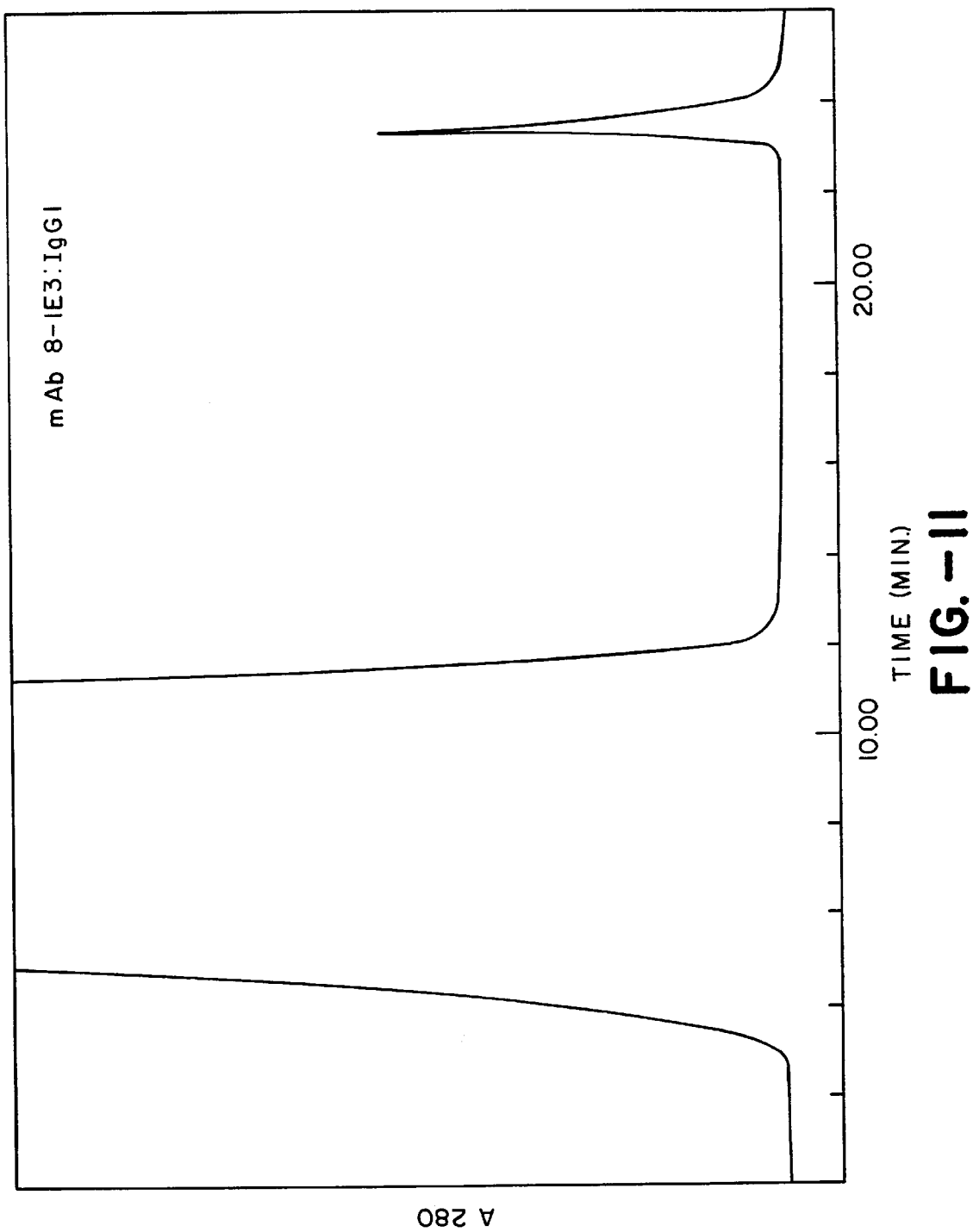

PROCESS FOR SEPARATING A SUBSTANCE FROM A MIXTURE

This is a continuation of application Ser. No. 08/949,448, filed Oct. 14, 1997, now abandoned which is a continuation of application Ser. No. 08/714,523, filed Sep. 16, 1996, now abandoned which is a continuation of application Ser. No. 08/397,414, filed Mar. 1, 1995, abandoned, which is a continuation of application Ser. No. 08/070,554, filed Jun. 1, 1993, abandoned, which is a divisional of application Ser. No. 07/682,393, filed Apr. 2, 1991, now U.S. Pat. No. 5,240,602, which is a continuation of application Ser. No. 07/485,866, filed Feb. 23, 1990, abandoned, which is a continuation of application Ser. No. 07/187,765, filed Apr. 29, 1988, abandoned, which is a continuation-in-part of application Ser. No. 07/058,988, filed Jun. 8, 1987, abandoned.

FIELD OF THE INVENTION

The present invention relates to chromatographic material which when covalently coupled to an appropriate affinity ligand can be used for the separation and/or detection of biological and other materials by way of high performance affinity chromatography (HPAC) or other separation or detection techniques.

BACKGROUND OF THE INVENTION

The coupling of various ligands to solid supports to form chromatographic agents reportedly has been accomplished by using relatively short, low molecular weight linkers or relatively long, high molecular weight linkers which inherently are hydrophilic because of their ionic properties or hydrophobic because of their non-ionic and nonpolar nature.

U.S. Pat. No. 4,532,232 to Larsson, et al. and U.S. Pat. No. 4,406,792 to Glad, et al. each disclose inter alia the coupling of a ligand to silica by way of the short length linker -glycidoxypropyltrimethoxy silane.

U.S. Pat. No. 4,415,665, to Mosbach, et al., reports the coupling of a substituted adenosine 5'-monophosphate to silica particles pretreated with 2,2,2-trifluroethanesulfonyl chloride or to porous silica gel substituted with —(CH$_2$)$_3$—O—CH$_2$—CH(OH)—CH$_2$OH— and pretreated with 2,2,2-trifluroethanesulfonyl chloride prior to coupling. Mosbach also reports the use of sulfonyl chlorides to couple specific proteins and a substituted adenosine 5'-monophosphate to polysaccharide derivatives, e.g., agarose and cellulose.

U.S. Pat. No. 4,431,554 to Atkinson, et al., reports the coupling of various organic dyes to silica by use of inter alia -glycidoxypropyltrimethoxy silane alone or in conjunction with a bifunctional aliphatic linker of relatively short length, e.g., 1,6 diamino hexane.

U.S. Pat. No. 4,177,038 to Biebricher, et al. states that low molecular weight polyethyleneglycol 200 can be used to couple biological material to a solid support by using organic diisocyanates to couple one end of the glycol to biological material and the other end to a cellulose support.

Biebricher also reports an example involving porous glass pellets, wherein -aminopropyltrimethoxy silane is first coupled to the porous glass pellets. Thereafter, the silane treated silica is reacted with tetramethylene diisocynate and then coupled to 3-aminophenyl boronic acid.

The coupling of ligands to solid support through specific water soluble or hydrophilic linkers is reported in U.S. Pat. No. 3,715,278 to Miller and U.S. Pat. No. 4,352,884 to Nakashima, et al. In Miller, a copolymer of ethylene and maleic anhydride was coupled to calcium silicate particles pretreated with -aminopropyltrimethoxy silane. The enzyme subtilisin was then coupled through the side chain carboxylic groups of the coupled polymer.

In Nakashima, et al., a copolymer of a hydrophilic acrylate or methacrylate and an unsaturated carboxylic acid or amine reportedly was used to coat the surface of a solid support apparently to minimize the non-specific adsorption of the support. Bio-active material was then coupled directly to the carboxyl or amino groups directly by carbodiimide condensation or indirectly through e-aminocaproic acid or diaminoheptane.

A significant disadvantage in the chromatographic agents of Miller and Nakashima, however, are the free carboxylic acid and amino groups of the copolymers which may remain after coupling of bio-active material. These chromatographic agents therefore may have significant residual ion exchange properties which may result in undesirable adsorption or adversely effect the properties of the bound bio-active material.

Other chromatographic agents which may have residual ion exchange properties and thus suffer from these same disadvantages include those disclosed in: U.S. Pat. No. 4,210,722 to Silver (copolymer containing β-hydroxyalkylamine); U.S. Pat. No. 4,415,663 to Symon, et al. (polyamine impregnated support); U.S. Pat. No. 4,132,596 to Meiller, et al. (cross-linked polymer containing tertiary amino groups or quarternary ammonium salts); U.S. Pat. No. 3,888,864 to Cleeland, Jr. et al. (linkage of aminoalkylethers of opium alkaloids to carboxylated latex particles); U.S. Pat. No. 4,451,568 to Schneider, et al. (copolymers of acrylic acid or derivatives thereof, e.g. aminoalkylmethacrylates); U.S. Pat. No. 4,438,196 to Lantero, Jr. (polyamine adsorbed on activated granular carbon); U.S. Pat. No. 4,610,962 to Takagi, et al. (regenerated cellulose fiber treated with polymer containing pendant carboxylic anhydrides); and U.S. Pat. No. 4,581,337 to Frey, et al. (latex particles coated with water insoluble copolymer treated with second copolymer having a polyetherpolyamine linker).

In addition, the use of various hydrophobic linkers have been reported. See for example, U.S. Pat. No. 4,071,409 to Messing, et al. (polymeric aromatic isocyanate linkers) and U.S. Pat. No. 4,007,089 to Smith III (asymmetric bifunctional saturated or unsaturated hydrocarbons as linker).

Many of the above described chromatographic agents are not suitable for chromatographic separations which utilize high linear flow rates (e.g., greater than about 0.1 c/min) and/or application of relatively high pressures (e.g., greater than about 200 psi). Thus, for example, derivatives of polysaccharides, e.g., cellulose, sepharose, agarose, etc., are not useful in such applications since they are relatively compressible.

Further, many solid supports which may be used in such high velocity/high pressure chromatography applications, e.g., cross-link sulfonated polystyrene, have demonstrated undesirable non-specific adsorption.

Accordingly, it is an object of the present invention to provide chromatographic material which is substantially free of reversible non-specific adsorption.

Further, an object of the present invention is to provide chromatographic material with substantially improved pH stability.

Still further, an object of the present invention is to provide a chromatographic material having improved binding kenetics.

Finally, it is an object herein to provide chromatographic material which is substantially non-compressible as evidenced by high linear flow rates greater than approximately 0.1 cm/min.

SUMMARY OF THE INVENTION

The present invention comprises chromatographic material having the general formula S-B-X, where S is a substantially non-compressible solid support, B is a binding group and X is a substantially non-ionic hydrophilic spacer. This chromatographic material is formed by covalently coupling the solid support through the binding group to the spacer.

The invention also comprises chromatographic material having the general formula S-B-X-Y-L where S, B and X are as previously described, L is an affinity ligand, and Y is a coupling group. The chromatographic material is formed by covalently coupling S-B-X as described and coupling said ligand to said spacer X through the coupling group Y.

The invention further comprises chromatographic material having the general formula S-B-X-Y' where S, B and X are as previously described and Y' is an activated coupling group. This chromatographic material is formed by covalently coupling S-B-X to Y'. This chromatographic material may then be used to covalently couple an affinity ligand L which is reactive with the activated coupling group to form the chromatographic material having the general formula S-B-X-Y-L.

In addition, the invention also comprises a process for the chromatographic separation of a substance from a mixture. The mixture containing the substance is first contacted with the chromatographic material described herein containing a ligand having an affinity for the substance of interest. The chromatographic material is thereafter washed with a solution to remove non-binding species of the mixture from the chromatographic material followed by the passing of an eluting solution through the chromatographic material to recover the bound substance.

The invention also comprises a process for the isolation and detection of at least one substance in a mixture utilizing the chromatographic material herein. The mixture containing the substance of interest is first contacted with the chromatographic material containing an appropriate affinity ligand. Thereafter, the presence of bound substance is determined qualitatively or quantitatively.

BRIEF DESCRIPTION OF THE DRAWINGS

FIG. 11 is a chromatogram depicting the purification of IgG from an IgG hybridoma supernatant on protein G silica.

DETAILED DESCRIPTION OF THE INVENTION

Figure 1:
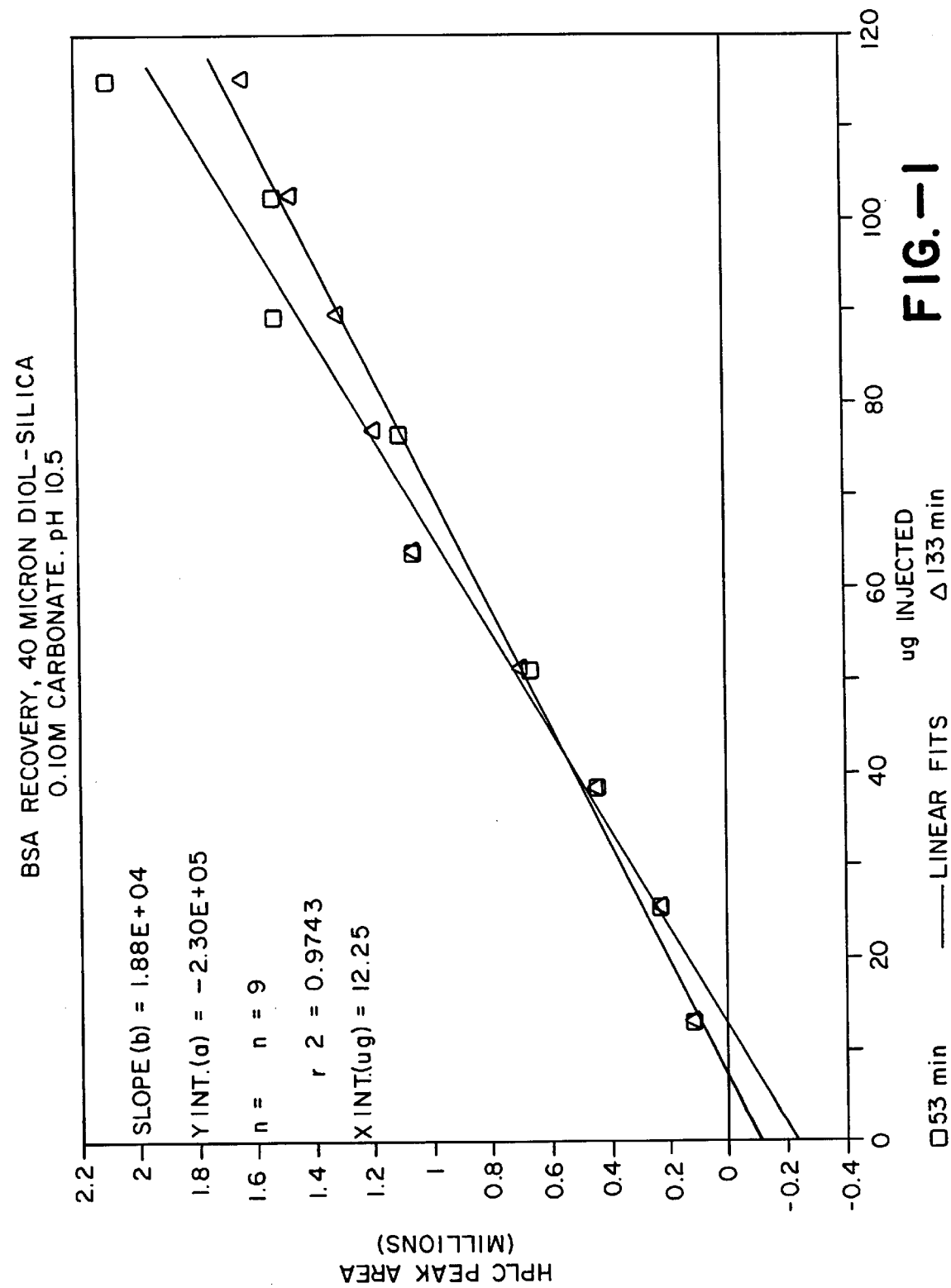
FIG. 1 depicts the recovery of bovine serum albumin from a column containing 40 micron diol silica after treatment with pH 10.5 buffer for 53 and 133 minutes.

The use of silica and other metal oxides, such as alumina, titania, etc. as solid support for chromatographic reagents for analytical and preparative separations of biological materials has not attained wide-spread acceptance. This is because such chromatographic reagents suffer from non-specific adsorption and instability in alkaline media which has been attributed to the metal oxide support. See, e.g., Carr, P. W., et al., *Chromatographic Forum* (September–October 1986) pp. 31–37. Such chromatographic agents are particularly undesirable if, for example, a biological material is being purified for therapeutic administration. For example, an antigen purified by a monoclonal antibody covalently attached to silica may be contaminated by protein which was non-specifically adsorbed during antigen binding and subsequently desorbed with the antigen. The antigen thus purified could produce an undesirable imunogenic response from the contaminating protein if administered to an animal or a human. In the case of human therapeutics, FDA approval could prove difficult or impossible to obtain.

Other solid supports such as cross-linked sulfonated polystyrenes, although stable to both high and low pH, are also plagued by non-specific adsorption.

To overcome these problems, the inventor has developed the chromatographic material of the present invention which is substantially free of reversible non-specific adsorption. In this chromatographic material, a substantially non-ionic hydrophilic spacer is interposed between a solid support and an affinity ligand.

Surprisingly, the chromatographic material containing silica as solid support also has a demonstrated pH stability heretofore unknown for chromatographic reagents utilizing silicon oxides.

In addition, the chromatographic material has demonstrated an increased binding capacity and increased adsorption rate constant as compared to a similar chromatographic reagent which does not utilize a substantially non-ionic hydrophilic spacer. The use of a non-ionic hydrophilic spacer appears to cause a significant increase in the amount of biological material which is adsorbed to the chromatographic material, thus minimizing the amount of biological material lost in the void volume.

It is believed that the use of non-ionic hydrophilic spacers allows greater steric access by bound affinity ligands to biomacromolecules, thus allowing a greater fraction of immobilized affinity ligands to interact with such biological molecules. Thus, in Example 12, the capacity of a silica (30 micron)-polyethylene glycol-Protein A column to bind IgG, utilizing a polyethylene glycol (PEG) hydrophilic spacer having an average length of about 45 atoms, was almost double that of a commercially sold Protein A column having the Protein A immobilized by means of a 7-atom (3-glycidoxypropyl linker) to silica (10 micron—Pierce Chemical Company). Similarly, in Example 13, the same silica-PEG-Protein A column demonstrated an adsorption rate constant for human IgG which was approximately 1.8 times greater than that of the commercially sold Protein A column.

The 1.8 fold increase in absorption rate constant is particularly surprising in light of the expected result that the larger particle silica should have an adsorption rate which is decreased in proportion to the cubed ratio of the particle diameters. Thus, the rate of the binding of IgG to the 30 micron Protein A PEG 600-silica compared to binding of IgG to the 10 micron Pierce Protein A silica is expected to be $1/(3)^3$ or $1/27$th of that of the 10 micron Pierce Protein A silica, all other parameters being the same. The 1.8 fold increase observed is therefore correctable to 27×1.8 which theoretically would result in a 48.6 fold increase in adsorption rate constant for the Protein A PEG 600 silica.

An example of the practical utility of a high speed chromatographic affinity support is the Protein A purification of monoclonal antibodies derived from mouse cells. Protein A is used for affinity purification of mouse IgG antibodies of the IgG 1, 2a, 2b ideotypes and human IgG 1, IgG 2 and IgG 4 subclasses. Unfortunately, mouse derived antibodies bind very poorly to Protein A at neutral pH ranges (Johnstone, A. and Thorpe, T., *Immunochemistry in Practice* (1982), pp. 209–212), unless the binding is done under highly basic pH conditions (0.1 M tris base; pH 9.5). Mouse monoclonal antibodies are of great commercial importance for immunopurification of proteins. The conditions of 0.1 M tris pH 9.5, used by many practitioners of the art works for Protein A Sepharose affinity supports which allows process cycle times of 4 to 6 hours. These conditions, however, cannot be applied to silica gel-based Protein A HPAC columns, due to the instability of conventional silica gel formulations at pH levels above 8.5. The novel and unexpected alkaline pH stability of the the PEG derivatized silica described herein allows rapid (10–20 minute cycle times) affinity chromatography of the industrially important mouse monoclonal antibodies which cannot be achieved by the Protein A Sepharose affinity supports.

"Chromatographic material" refers to material containing a substantially non-ionic hydrophilic spacer covalently coupled at one end to a solid support alone or in combination with an affinity ligand covalently attached via a coupling group to the other end of the substantially non-ionic hydrophilic spacer. Chromatographic material also refers to material containing the substantially non-ionic hydrophilic spacer covalently coupled at one end to a solid support and at the other end to an "activated coupling group" which is used to couple a desired affinity ligand to the non-ionic hydrophilic spacer. The solid support may be "substantially noncompressible" as defined hereinafter or may be a solid support not comprising a polysaccharide or derivative thereof.

As used herein, "chromatographic separation" refers to a chromatographic technique for separating at least one substance from a mixture which employs chromatographic material having an affinity ligand for such a substance covalently attached to a solid support by way of a non-ionic hydrophilic spacer. Such chromatographic separation is typically by way of "high performance affinity chromatography" (HPAC) and involves (1) contacting the mixture with the chromatographic material containing an appropriate affinity ligand for a desired substance, (2) washing the chromatographic material to remove non-binding species, and (3) eluting the bound substance from the chromatographic material. Generally, HPAC is practiced using relatively high pressures (e.g. greater than 500 psi) and relatively high linear flow velocities (e.g., greater than approximately 0.1 cm/min).

"Separation and detection" of at least one substance in a mixture refers to a technique which employs chromatographic material containing an affinity ligand for a particular substance to be detected. Generally, the chromatographic detection is carried out by (1) contacting the mixture containing the substance to be detected with the chromatographic material containing the appropriate affinity ligand, (2) washing the chromatographic material to remove non-binding species, and (3) contacting a detection solution with the chromatographic material to detect the substance retained. When so used, the chromatographic material containing the affinity ligand may comprise beads, microspheres, dipsticks or other appropriate forms or may comprise the inner surface of a microtitre plate or test tube. The detection solution typically contains an antibody or other molecule capable of recognizing the substance bound to the chromatographic material (e.g., RNA or single stranded DNA to detect complementary strands) and is conjugated with either a radioactive label or an enzyme. The chromatographic material is thereafter contacted with a second washing solution to remove nonreactive conjugate from the chromatographic material. Thereafter, the amount of substance bound to the chromatographic material can be determined by measuring the amount of radioactivity bound to the chromatographic material or by the extent of the chemical reaction mediated by bound conjugate enzyme. Alternatively, a competitive or other assay known to those in the art may be employed with the chromatographic material of the invention.

An "affinity ligand" is any ligand which when covalently attached to the chromatographic material provides the capability of specifically interacting with one or more substances of interest. When used as a chromatographic material for chromatographic separation it is capable of separating substances such as biological molecules from a mixture containing such molecules, thus permitting their isolation and purification. Such chromatographic material, however, may also be used as a diagnostic reagent. When so used, the affinity ligand is capable of a similar interaction with specific biological molecules and when combined with methods known to those skilled in the art, permits the detection and/or quantitation of such biological molecules.

Affinity ligands of the present invention together with their known or anticipated applications are listed in Table 1. This listing of affinity probes and their applications is presented by way of example only, there being many other potential affinity probes which could be used in practicing the present invention. In this regard, it is to be understood that the affinity ligands comprising proteins and polypeptides include such molecules and (1) naturally occurring allellic variations that may exist or occur in the amino acid sequences of such polypeptides or proteins and (2) variations in the amino acid sequences of such proteins and polypeptides brought about, for example, by way of recombinantly engineered mutagenesis wherein various deletions, insertions and/or substitutions of one or more of the amino in such amino acid sequences are produced or variations in such polypeptides and proteins brought about by way of classical mutagenesis of the organisms producing such affinity ligands.

For example, the affinity ligand Protein G is a naturally occurring protein isolated from Streptococcus which is known to bind albumin and IgG. Protein G, however, has been cloned such that recombinant Protein G can be obtained from recombinant microorganisms capable of expressing this protein. Fahnestock S. R. et al., (1986) *J. Bact,* 167, 870–880. In addition, the gene sequence of protein G has been modified by recombinant techniques to alter the specificity of Protein G for albumin. In particular, the albumin binding capacity of this molecule has been substantially modified by deleting the albumin bending regions A1 and A2. In addition, the C-terminal membrane anchor region has been deleted with the lysine rich C-repeat region being retained. See Fahnestock S. R. (1987) *Trends in Biotechnology,* 5, 79–83 and Newly Available Immunosorbant: Recombinant Modified Streptococcal Protein G by Fahnestock S. R. in *Biofutur,* January 1988. This modified Protein G is commercially available from Genex Gaithersburg Maryland under the trandename GammaBind G Type 2.

Solid supports which may be used in practicing the invention include the metal oxides of silicon, titanium, aluminum, vanadium, zirconium and the like, including various ceramics known to those skilled in the art. In addition, various polymeric resins such as cross-linked polystyrenes and polymethacrylates may be used as solid supports.

One characteristic of solid supports relates to their compressibility. In other words, as the applied pressure is increased to a particular solid support in a chromatographic column an increase in flow rate is observed over the useful pressure range of the particular solid support. For each solid support, there is a critical pressure above which an increase in pressure will not produce an increase in flow rate and in some instances may cause a decrease in the observed flow rate.

A "substantially non-compressible" solid support is a support which maintains an increase in flow rate with an increase in pressure above about 500 psi. Examples of such solid supports include silica, titania, alumina, vanadia, cross-linked sulfonated or nitrated polystyrene and the like. In addition to these preferred solid supports, other non-compressible solid supports include those which maintain an increase in flow rate commensurate with an increase in pressure above about 200 psi. Included in this group are the above mentioned solid supports having positive flow characteristics above 500 psi and supports including polymethacrylates and copolymers thereof.

Solid supports may also be defined by their flow characteristics. Thus, chromatographic material using solid supports that result in linear flow rates of greater than 0.1 cm/min (e.g., methacrylates) and preferably greater than 100 cm/min (ceramics and oxides of silicon, aluminum, titanium, vanadium, etc.) are solid supports as used herein.

As used herein, "polysaccharides and derivatives thereof" include cellulose, Sephadex, Sepharose, agarose and the like. These supports cannot maintain adequate flow rates above about 3–30 psi due to the ease with which they are compressed at such pressures.

In some instances, the choice of pore size of the solid support can effect the performance of the chromatographic material. Thus, for example, when Protein A is coupled to silica via a PEG molecule, it was found that silica having a pore size of approximately 500 Angstroms demonstrated an increased adsorption rate constant as compared to a commercially available Protein A column (Example 13). This increase in adsorption rate constant, however, was not observed when silica having pore size of 60 Angstroms was used to couple Protein A via a PEG molecule. Pore size of the solid support, thus, is a parameter which may be varied to maximize the performance of a particular chromatographic material for a specific application.

TABLE 1

Affinity Chromatography Ligands

| No. | Affinity Ligand | Applications |
|---|---|---|
| 1 | Boronic Acid | Carcinogen metabolites, cathecholamines, nucelosides, sugars, adenylate cyclase |
| 2 | Iminodiacetic acid | Metaloproteins, interferons |
| 3 | Quinacrine | Concanavalin A, DNA, RNA |
| 4 | Acridine | DNA, RNA |
| 5 | Sulfhydryl | Transfer RNA, active subtilisin |
| 6 | Protein A | Antibody purification, IgG antibodies Fc fragments |
| 7 | Dinitrophenyl | Antibody purification, mechanisms |
| 8 | Cibacron blue | Monoclonal antibodies, serum globulin, enzyme purification |
| 9 | Herparin | Thrombospondin, ATPase |
| 10 | Gelatin | Fibronectin |
| 11 | Concanavalin A | Glycoproteins, interferons |
| 12 | Monoclonal and polyclonal antibodies and fragments thereof | Antigen immunoaffinity purification |
| 13 | Lectins | Glycoproteins |
| 14 | Poly (U) | messenger RNA |
| 15 | Poly (A) | messenger RNA |
| 16 | Lysine | Plasminogen activator, rRNA, DNA |
| 17 | 5' AMP | NAD+ requiring enzymes |
| 18 | 2', 5' ADP | NADP+ requiring enzymes |
| 19 | Affi-Gel blue | Monoclonal antibodies, enzyme purification, blood proteins |
| 20 | Organomercurial | Histones |
| 21 | Procion Red dye | Interferons |
| 22 | Biotin | Avidin |
| 23 | Avidin | Biotinylated probes |
| 24 | Calmodulin | Activated enzymes, antibodies |
| 25 | Activated supports | Protein coupling, immunoaffinaity of: interferon TPA, antigens, fibrinogen |
| 26 | Oligo dT | Messenger RNA, DNA |
| 27 | Triphenylmethyl | FMOC protected peptides and dimethylxytrityl (DMT) protected polynucleotides |
| 28 | Naphoyl compounds | FMOC protected peptides and dimethylxytrityl (DMT) protected polynucleotides |
| 29 | Antigens | Purification of polyclonal and monoclonal antibodies |
| 30 | Protein G | Antibody purification, IgG antibodies, Fc fragments |

A "substantially non-ionic hydrophilic spacer" is covalently interposed between the solid support and affinity ligand. This spacer may be any polymer of subunits which when polymerized produces a spacer containing polar but non-ionized moieties which renders the spacer hydrophilic.

It includes spacers such as polyethylene glycol, polyvinyl alcohol, polypropylene glycol, polyethylene dithiol, poly(2-hydroxyethylmethacyrlate), poly(ethylene succinate) and poly non-ionic polar amino acids such as polymers of glycine, serine, threonine, cysteine, tyrosine, asparagine glutamine and combinations thereof. Such spacers preferably have a backbone length of at least about 12 atoms, preferably about 18 atoms and most preferably about 45 atoms.

These spacers may be as long as about 1200 atoms or more but are preferably not longer than about 500 atoms, most preferably about 90–100 atoms. Thus, the following polymers having the indicated degree of polymerization may be used as non-ionic hydrophilic spacers.

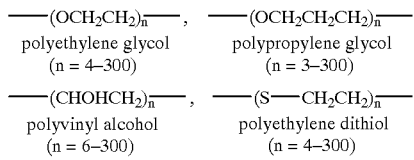

Polyethylene glycol is the preferred non-ionic hydrophilic spacer used to practice the invention. Polyethylene glycol is available from chemical supply houses and is generally marketed on the basis of average molecular weight. Thus, Aldridge Chemical markets PEG having average molecular weights of 200 (mixture of 4-mer and 5-mer), 300, 400, 600, 1000, 1450, 2000, 3400, 8000 and 14000 daltons. Of these polyethylene glycols, those having molecular weights between 600 and 1450 daltons are preferred.

As used herein a "binding group" is any bifunctional agent which is capable of covalently coupling the non-ionic hydrophilic linker to the solid support. As such, the choice of binding group is primarily determined by the nature of the solid support and the non-ionic hydrophilic linker. Preferred binding groups include those which produce the chemical linkages as hereinafter described for organic couplers. When ceramics or oxides of silicon, aluminum, titanium, zirconium, vanadium and the like are the solid support, a preferred binding group is

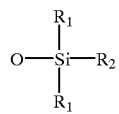

wherein $R_1$ equals OH, alkyl, substituted alkyl, alkyl oxide, and silicon, and $R_2$ equals substituted alkyl, diol, ether, alkyl carboxy, alkyl thiol, and alkyloxy. Preferred binding groups of this type include haloalkyltrichloro silane, isocyanatoalkyltrialkoxy silane and most preferrably glycidoxyakyltrialkoxy silane.

As used herein, a "coupling group" is used to covalently couple the affinity ligand to the non-ionic hydrophilic spacer and/or to covalently attach the hydrophilic non-ionic spacer to the solid support. Thus, Y may be selected from the group consisting of the following chemical linkages.

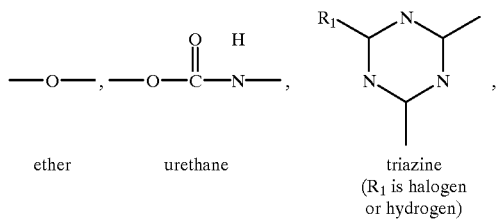

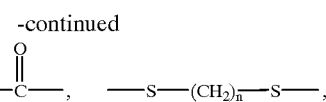

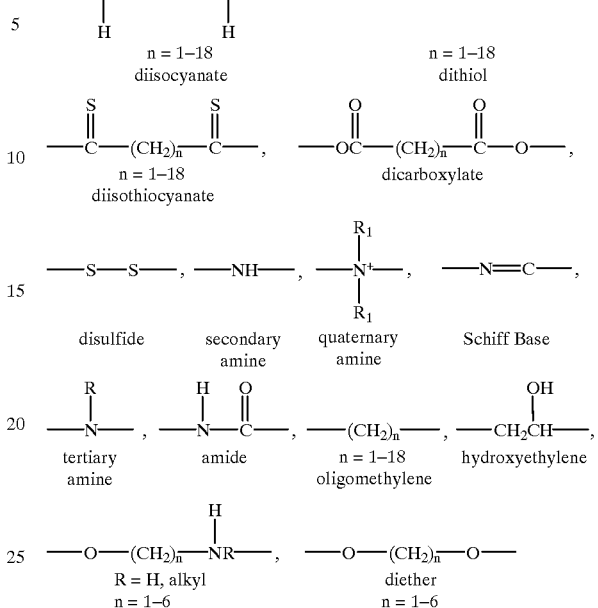

or any combination of two or more of the above Y groups. The choice of chemical reagent to form such coupling groups will depend on the particular ligand and non-ionic hydrophilic linker used. It is to be understood that the coupling group Y may comprise one or more atoms from the hydrophilic spacer and/or affinity ligand. Thus, a chemical reagent such as methane sulfonyl chloride may be used to couple the terminal carbon of a polyethylene glycol to a primary or secondary anine on an affinity ligand to from a secondary or tertriary amino coupling group.

As used herein, an "activated coupling group" refers to a chemically reactive moeity covalently coupled to the non-ionic hydrophilic spacer coupled to the solid support. Such activated coupling groups are used to form the above chemical linkages used to covalently attach the affinity ligand to the non-ionic spacer through the coupling group. Chromatographic material containing such an activated coupling group is sometimes referred to as "activated chromatograpic material".

Table 2 exemplifies various pathways by which activated chromatographic material S-B-X-Y' containing the activated coupling group Y' can be formed and subsequently used to couple various affinity ligands to form the chromatographic material S-B-X-Y-L. In this table the non-ionic hydrophilic linker X is PEG coupled to silica solid support S. It, of course, will be appreciated that this table is presented by way of example only and that other solid supports, non-ionic hydrophilic linkers and activation reagents may be used depending upon the particular application of the chromatographic material.

TABLE 2

| Chromatographic Material S-B-X | Activation Reagent | Activated Chromatographic Material S-B-X-Y* | Affinity Ligand | Chromatographic Material S-B-X-Y-L |
|---|---|---|---|---|
| Silica-PEG | imidazole-C(=O)-imidazole (CDI) | Silica-PEG–O–C(=O)–(imidazole) | L-NH$_2$ | Silica-PEG–O–C(=O)–NH–L |
| | 1-methyl-2-fluoropyridinium tosylate | Silica-PEG–O–(pyridinium-CH$_3$)[TsO$^-$] | L-NH$_2$ | Silica-PEG–NH–L |
| | CNBr | Silica-PEG–[–O–CN] | L-NH$_2$ | Silica-PEG–O–C(=O)–NH–L |
| | 4-nitrophenyl chloroformate | Silica-PEG–O–C(=O)–O–(4-NO$_2$-C$_6$H$_4$) | L-NH$_2$ | Silica-PEG–O–C(=O)–NH–L |
| | N-hydroxysuccinimidyl chloroformate | Silica-PEG–O–C(=O)–O–(N-succinimidyl) | L-NH$_2$ | Silica-PEG–O–C(=O)–NH–L |
| | ClSO$_2$CH$_2$CF$_3$ | Silica-PEG–O–S(=O)–O–CH$_2$–CF$_3$ | L-NH$_2$ | Silica-PEG–NH–L |

TABLE 2-continued

| Chromatographic Material S-B-X | Activation Reagent | Activated Chromatographic Material S-B-X-Y* | Affinity Ligand | Chromatographic Material S-B-X-Y-L |
|---|---|---|---|---|
| | $ClSO_2CH_3$ | Silica-PEG[—O—S(=O)—O—CH$_3$] | L-NH$_2$ | Silica-PEG—N(H)—L |
| Silica-PEG | DMSO/Acetic Anhydride | Silica-PEG [—CHO] | L-NH$_2$ + NaCNBH$_3$ | Silica-PEG—CH$_2$—N(H)—L |
| | 1) DMSO/Acetic Anhydride 2) Hydrazine | Silica-PEG[—C(H)=N—NH$_2$] | L-CHO | Silica-PEG—C(H)=N—N=C(H)—L |
| | Oxidant | Silica-PEG [—COOH] | L-NH$_2$ + carbodiimide | Silica-PEG—C(=O)—N(H)—L |

* Brackets designate activated coupling groups Y'

Preferred Embodiments

The following preferred embodiments of the invention are presented by way of example and do not expressly or impliedly limit the scope of the invention.

Preparation of Chromatographic Material

EXAMPLE 1

40 Micron Epoxy Silica

Silica gel (Woelm, 40 micron, 100 g) was placed in a 1 liter round bottom flask and dried in an oven controlled at 150° C. for 12 hours. The flask was removed from the oven, stoppered, and cooled to room temperature. Methanol (Karl Fischer grade, 1 l), 4.1 ml water, and 16.6 ml trimethoxyglycidoxy silane (Petrarch Chemicals) were added to the silica. The flask was agitated for 24 hours by a slow rotation. The mixture was filtered through a coarse fritted glass funnel and washed three times each with 200 ml portions of methanol, water, methanol, and ether. After the ether wash, the resultant epoxy silica gel was dried by suction on the funnel for 1 hr. The silica was then dried in an oven at 100° C. for 1 hour.

EXAMPLE 2

10 Micron Bromopropyl Silica

Silica gel (Vydac, 10 micron, 10.0 g) was placed in a 500 ml round bottom flask and dried in an oven controlled at 150° C. for 12 hours. The flask was removed from the oven, stoppered, and cooled to room temperature. Toluene (100 ml), methanol (0.67 ml), and 1.20 ml of trichlorobromylpropyl silane (Petrarch) was added in three portions with vigorous swirling of the flask between additions. The flask was then agitated by rotation for 12 hours at room temperature. The reaction mixture was filtered on a coarse fritted glass funnel and washed three times each with 100 ml portions of methanol, ether, methanol, and ether. After the ether wash, the resultant bromopropol silica gel was dried by suction on the funnel for 1 hour. It was then dried in an oven at 100° C. for 1 hour.

EXAMPLE 3

40 Micron PEG 600-Epoxy-Silica

The epoxy silica (40.0 g), prepared by the method of Example 1, was placed in a 250 ml rb flask and 180 g of polyethylene glycol 600 (Aldrich Chemicals) having a length of approximately 45 atoms (15-mer) was added. The flask was heated to 150° with slow rotation for two hours. The flask was cooled to ambient temperture and 4.82 g ethylene glycol monomethyl ether was added and the flask was heated to 150° for one more hour. The mixture was cooled to room temperature and the paste was dissolved in methanol. The mixture was filtered on a coarse fritted glass funnel and washed three times each with 100 ml portions of methanol, 10% acetic acid, water, methanol, and ether. After the ether wash, the resultant PEG 600 silica gel was dried by suction on the funnel for 1 hour. The silica was then dried in an oven at 100° C. for 1 hour.

EXAMPLE 4

40 Micron PEG 600-Propyl-Silica

Bromopropyl silica (40.9 g), prepared by the method of Example 2 using 40 micron silica, and 350 ml dioxane were added to a 3 neck 350 ml round bottom flask equipped a dry nitrogen inlet and a mechanical stirrer and a distillation apparatus that also served as a reflux condensor. 55 g of PEG 600 (Aldrich) and either 9.23 g (15-Crown-5) or 13.5 g tetrabutylammonium bromide (Sigma) were added and the mixture was agitated with a stirring motor. The flask was heated to boiling and approximately 50 ml of solvent were distilled away to remove water by azeotropic distillation. The mixture was cooled to ambient temperature and 2.53 g sodium hydride (60% suspension in mineral oil) was added. When hydrogen evolution ceased, the mixture was refluxed for two hours. The flask was cooled to room temperature and the reaction mixture was filtered on a coarse fritted glass funnel and washed three times each with 100 ml portions of methanol, ether, methanol, and ether. After the ether wash, the resultant PEG 600-propyl-silica gel was dried by suction on the funnel for one hour. The PEG 600-propyl-silica was then dried in an oven at 100° C. for one hour.

EXAMPLE 5

30 Micron 500 Angstrom Pore PEG 600-Propyl-Silica

Amicon Matrex 500 Å pore silica gel was derivatized with trichlorobromopropyl silane in pyridine by the method of Example 2. This bromopropyl silica was then treated with polyethylene glycol 600 by the method of Example 4.

EXAMPLE 6

40 micron Napthoyl-PEG 600-Silica

PEG 600-epoxy-silica (3.04 g) prepared by the method of Example 3 was placed in a 100 round bottom flask and heated to 100° for one hour. The flask was cooled with a drying tube attached. Pyridine (30 ml) which had been dried over calcium hydride was added and the silica was suspended by placing the flask in a bath sonicator. Napthoyl chloride (31 mg, 0.16 mmole) was added and the mixture was swirled rapidly for 1 minute and slowly for 2 hours. The reaction mixture was filtered on a coarse fritted glass funnel and washed three times each with 100 ml portions of methanol, ether, methanol, and ether. After the ether wash, the resultant napthoyl-PEG 600-silica gel was dried by suction on a funnel for 1 hour.

EXAMPLE 7

Carbonyl Diimidazole (CDI)-PEG 600-Epoxy-Silica

PEG 600-epoxy-silica (3.0 g) was suspended in 30 ml dioxane in a 100 ml round bottom flask. Carbonyl diimidazole (CDI) (0.365 g, 0.25 mmol, Sigma) was added and the suspension was agitated while heating to 50° for 30 minutes. The CDI activated silica gel was filtered on a coarse fritted glass funnel and washed two times each with 100 ml dioxane and 100 ml ether. The gel was dried by suction on the funnel for one hour.

EXAMPLE 8

Phenyl Boronic Acid (PBA)-PEG 600-Silica

CDI-PEG 600-epoxy-silica (10.0 g) prepared by the method of Example 7 was placed in a 100 ml round bottom flask. 30 ml of 0.1 M phosphate buffer (pH 7.5) and 0.419 g of meta-aminophenyl boronic acid hemisulfate (Aldrich) was added and the mixture was agitated for two hours at room temperature. The reaction mixture was filtered on a coarse fritted glass funnel and washed three times each with 100 ml portions of water, methanol, ether, methanol, and ether. After the ether wash, the resultant PBA-PEG 600-silica gel was dried by suction on the funnel for one hour.

EXAMPLE 9

Protein A-PEG 600-Propyl-Silica

PEG 600-propyl-silica (1.0 g) prepared by the method of Example 5 was activated by CDI by the method of Example 7. The dry CDI activated silica was then suspended in 4.0 ml of 0.10 M sodium phosphate buffer (pH 7.4) containing 10.0 mg Protein A (Repligen). The suspension was swirled at ambient temperature for two hours. Ethanol anine (20 μl) was added and the silica swirled for an additional 30 minutes. Thereafter, the silica gel was filtered to remove unreacted protein and CDI and was then packed into an HPLC column by the upward slurry packing method.

EXAMPLE 10

40 Micron Bromopropyl Silica

Dried silica gel (200 g) was added into a three necked 2 liter round bottom flask. Anhydrous pyridine (1.31 liter) was charged into the round bottom flask. Bromopropyltrichlorosilane (33.0 ml, 0.2 mole) was dissolved in 200 ml pyridine (anhydrous), and added into the round bottom flask over a 30 min. period with stirring. At the end of addition, the mixture was stirred for 1 hour at room temperature. The liquid phase was removed by vacuum filtration on a scintered glass funnel. The gel was washed sequentially with toluene, acetonitrile:water (9:1), water, methanol, and ether. The dried gel was cured at 100° C. for 2 hours.

EXAMPLE 11

Alternative Preparation of 40 Micron PEG 600-Propyl-Silica

Polyethylene glycol (250 ml) was charged into a 1 liter round bottom flask. NaH in molar equivalence to the bromide content of the bromopropyl silica prepared as described in Example 10 was added into the flask. The flask was rotated at 125° C. for 6 hours. Liquid phase was removed by vacuum filtration. Silica was washed sequentially with methanol, water (45° C.), 2% acetic acid water (45° C.), methanol, and ether. The dried gel was cured at 1000 for 2 hours. This 40 micron PEG 600-Propyl Silica was used to prepare the aldehyde activated PEG Silica of Example 13 and the CDI-activated PEG 600 Silica used in Example 12.

EXAMPLE 12

Ovalbumin-Hydrazine-PEG 600-Silica

Hydrazine (0.44 ml) dissolved in 11 ml methanol was added to CDI-activated PEG 600 silica. The reaction vessel was placed on a wrist and shaken for two hours at ambient temperature. Liquid phase was removed by vacuum filtration on a scintered glass funnel. Silica was washed extensively with methanol and dried over vacuum. Chicken ovalbumin, a glycoprotein, was prepared for coupling by mild periodate oxidation of hydroxyl groups in the carbohydrate moiety to aldehyde functionalities. Ovalbumin (22 mg) was dissolved in 2 ml of 0.1 M Na acetate, pH 5.6, containing 0.15 M NaCl. Then, 10 μl of 0.25 M Na periodate was added to the dissolved glycoprotein. The reaction was allowed to proceed for 10 min. at ambient temperature with magnetic stirring, then stopped by adding 100 μl ethylene glycol. Buffer exchange into 2% acetic acid was accomplished by Sephadex G-50 chromatography. The oxidized ovalbumin at concentration of 5 mg/2 ml 2% acetic acid, was added to the hydrazine PEG 600 silica. After two hours at ambient temperature with shaking, the coupling reaction was stopped by removing the liquid phase on a scintered glass funnel. The silica was packed into a 10×0.46 cm HPLC column.

EXAMPLE 13

Aldehyde Activated PEG Silica

Aldehyde activated PEG silica was prepared by the controlled oxidation of the terminal alcohol group on the PEG by Moffit oxidation. Fourty micron P600 silica (40.0 g) was suspended in 160 ml DMSO (Aldrich, dried over 4A molecular sieve) in a 500 ml round bottom flask and vacuum was applied to the mixtur until bubbling ceased. Acetic anhydride (4.0 ml, 42.4 mmol) was then added and the mixture was again vacuumed for 2 minutes. The suspension was then mixed by gentle rotation in the round bottom flask at toom temperature for 2.0 hours. The aldehyde activated silica was worked up by pouring into a 350 ml fritted glass funnel and washed with 160 ml dioxane (3 times), 160 ml ether, and then air dried on the filter funnel.

EXAMPLE 14

Protein G Silica

The aldehyde activated silica of Example 13 (1.0 g) was suspended in a 50 ml round bottom flask in 4.0 ml of 0.1 M sodium citrate buffer, pH 3.5, containing 10.0 mg of Protein G (Genex, GammaBind G Type 2). The suspension was vacuumed for 2 min. and sodium cyanoborohydride (20.0 mg, 0.032 mmol) was added. The flask was evacuated for 2 min. and rotated for 30 min. at room temperature to complete the coupling reaction. The reaction was terminated by pouring the suspension into a fritted glass funnel and washing silica with 0.1 MNa phosphate buffer, pH 7.4. The silica was packed into a 10×0.46 cm HPLC column at 2500 psi.

EXAMPLE 15

Anti-BSA Antibody Silica

The aldehyde activated silica of Example 13 (1.0) was suspended in a 50 ml round bottom flask in 4 ml of 0.1 M sodium citrate buffer, pH 3.5, containing 8.5 mg affinity purified anti-BSA antibody (purified from rabbit anti-bovine albumin IgG fraction, [Organon Teknika, Cappel Div.] on a BSA column). After vacuuming the silica, antibody and buffer mixture for 2 min., sonicated for 2 min. and agitated on a wrist shaker for 1 hour. The silica was washed three times with 5 ml water. Five ml of 0.1 M sodium citrate buffer, pH 3.5 containing 250 mg glucosamine was added to the silica. After adding 10 mg of sodium cyanoborohybride the mixture was sonicated for 2 min. and then agitated for 20 min. on a wrist shaker. The silica was packed into a 10×0.46 cm column.

HPAC Chromotography

The chromatographic material (typically 1.1 gram) was packed in polished 3/16" stainless steel columns (100 mm by 4.6 mm I.D.) using the upward slurry packing technique of P. A. Bristo, et al., *J. Chromatography* 1977, 131, 57. All chromatographic procedures were performed at ambient temperatures (23–25° C.). The pumping system comprised three Waters Model 510 pumps controlled by Waters Model 680 gradient controller. The system was equipped with a Model 710B autosampler and a Waters Model 481 spectrophotometric detector. The data were collected by a Nelson analytical A/D converter and analyzed on a Hewlett-Packard 300 computer using Nelson analytical HPLC software.

EXAMPLE 16

Alkaline Degradation and Non-Specific Adsorption of Diol-Silica

It is well known in the art of silica based chromatography that exposure of silica gel and bonded silica gels to alkaline pH conditions results in solubilization of the silica gel. In the case of bonded silica gels with, for example C-18 chains linked by siloxane (Si—O—Si) bonds, the siloxane bond is attacked by the hydroxide ion. In this Example and Example 16 the alkali resistance of PEG 600-propyl-silica was compared to that of diol-silica prepared by acidic hydrolysis of epoxy silica prepared by the method of Example 1.

The effects of alkali on the PEG 600-propyl-silica and diol-silica were compared by observing excessive back pressure buildup in HPLC columns packed with the silica and eluted with pH 10.5 buffer. An increase in back-pressure with exposure to alkaline conditions indicates that the silica is being solubilized by the alkali.

In addition to observing increased back-pressure, non-specific binding was probed by measuring the interaction of the silica with bovine serum albumin (BSA).

This Example and Example 17 describe the observed back-pressure and recovery of BSA from diol-silica and PEG 600-propyl-silica after exposing the diol and PEG 600 silicas to pH 10.5 for various time periods. BSA recovery was measured by injecting increasing amounts of BSA (4–128 micrograms) into the HPLC column and measuring the peak area of the eluted BSA. Linear regression analysis of the peak area response vs. the BSA dose injected will show a linear plot with a vanishing x-intercept if the recovery of the BSA from the column is high. If small amounts of BSA are retained by the column, the x-intercept of the regression plot will be>0. The amount of the nonspecific BSA binding is measured by the x-intercept derived from the regression plot.

An HPLC column was packed with 40 micron diol-silica prepared by pH 3 hydrolysis of epoxy silica, prepared as in Example 1, with the upward slurry packing apparatus. The column was fitted with Valco end fittings and connected to the HPLC instrument. The column was measured for recovery of bovine serum albumin (BSA) by injecting 0.1 molar carbonate buffer with pH adjusted to 10.5 with 1 M sodium hydroxide. This buffer was placed in the reservoir to one of the pumps and was pumped through the column at the rate of 2 ml per minute. A solution of BSA was prepared and injected as described above. The experiment was terminated after 5.5 hours when it was noted that the back pressure on the column had grown to 2000 psi indicating significant solubilization of the silica. The results shown in FIG. 1 also show that significant amounts of BSA were retained non-specifically on the column.

EXAMPLE 17

Alkaline Stability of PEG 600-Propyl-Silica

Figure 2:
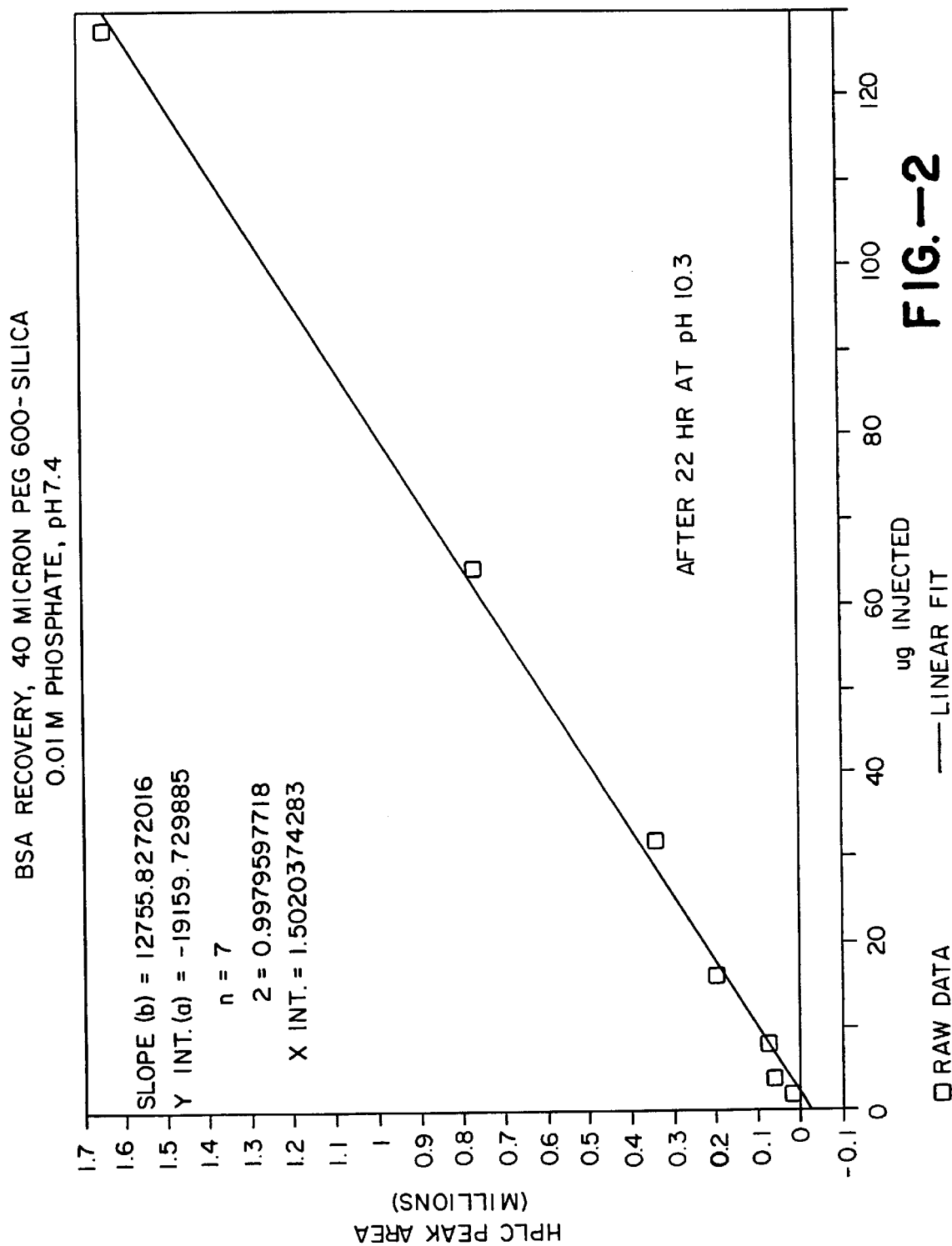
FIG. 2 depicts the recovery of bovine serum albumin from a column containing 40 micron silica coupled with polyethylene glycol 600 after treatment with pH 10.5 buffer for 22 hours.

The experiment was conducted as in Example 16 except that a column with the PEG 600-propyl-silica prepared by the method of Example 4 was used. pH 10.5 carbonate buffer was pumped through the column for 22 hours 2 ml/min. At that time samples of BSA varying from 2 to 128 micrograms were injected in the column and the peak areas were measured. The graph of the peak areas vs. injection amount is shown in FIG. 2. This figure shows that even after 22 hours of exposure to alkali, the recovery of BSA is greater than 99%. This indicates that the PEG 600-propyl-silica does not substantially adsorb BSA non-specifically and that the linkage of PEG 600 to silica is stable at high pH. In addition, it was noted that the back pressure on the column had not grown appreciably over the initial 600 psi back pressure that existed when the column was first operated.

EXAMPLE 18

Human IgG Binding Capacity of Protein A-PEG 600-Propyl-Silica

Figure 3:
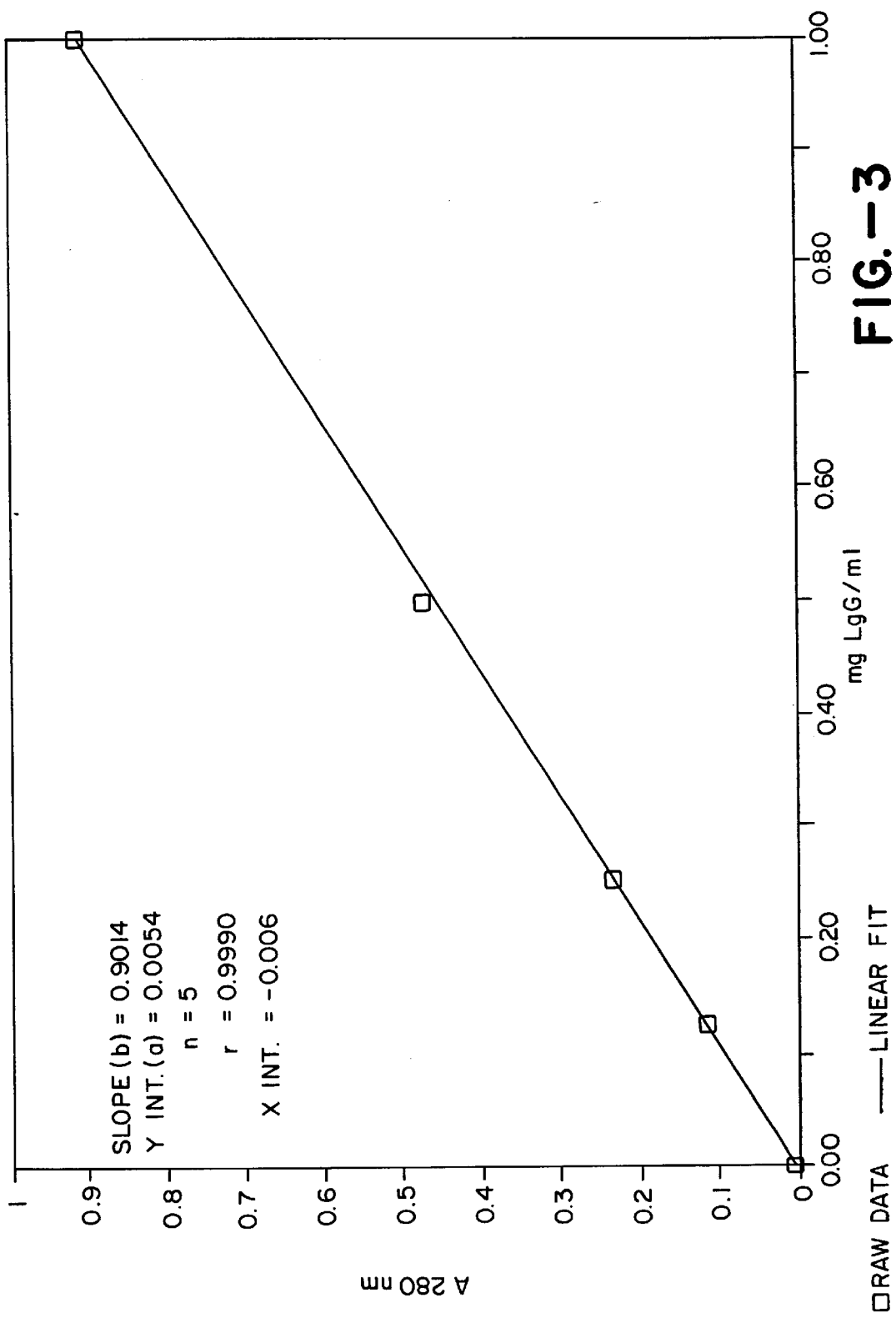
FIG. 3 is a calibration curve for determining the amount of IgG recovered from a column containing Protein A coupled to PEG-silica.

To determine the capacity of the Protein A-PEG 600-propyl-silica (Example 9), a column containing this chromatographic material was washed for 15 minutes with 2% acetic acid at a flow rate of 2 ml/min and then equilibrated for 15 minutes with 0.1M phosphate (pH 7.4) at 2 ml/min. A solution of human IgG (1 mg/ml) was pumped through this column at ½ ml/min and the absorbance at 280 nanometers of the column eluate was monitored until it rose to a constant level. At that point the column was judged to be saturated with the IgG and the column was washed with 30 column volumes of 0.1 molar phosphate buffer (pH 7.4). The IgG was then desorbed from the column by pumping through a solution of 2% acetic acid and collecting the eluate of the column. The effluent was collected, and the IgG was quantified by comparison of the 280 nm absorbance of the effluent with that of a calibration curve (FIG. 3) prepared by dissolving known amounts of IgG in 2% acetic acid.

The effluent volume was 23.0 ml and the A280 was 0.841. Using the regression coefficients in the calibration curve the concentration of IgG in the effluent was 0.927 mg/ml and the IgG capacity was 23.0×0.927 21.3 mg IgG/Column.

To compare this column with a silica column with the same pore size (500 Å) and protein A linked by a short 7-atom linker, the same IgG capacity experiment was performed with a Pierce Protein A column containing the same amount of silica and the same approximate surface area. The capacity of this column was found to be approximately 12 mg IgG/column.

EXAMPLE 19

It has also been determined that chromatographic materials containing non-ionic hydrophilic spacers have greater adsorbtion rate constants.

It is well known in physical chemistry that increasing the number of degress of freedom available to a reactant will decrease the entropic requirement of a bimolecular chemical reaction. The spacer molecules of the invention were used to give spacer-coupled affinity probes greater degrees of freedom than are available to affinity probes coupled with relatively short linker molecules.

Figure 4:
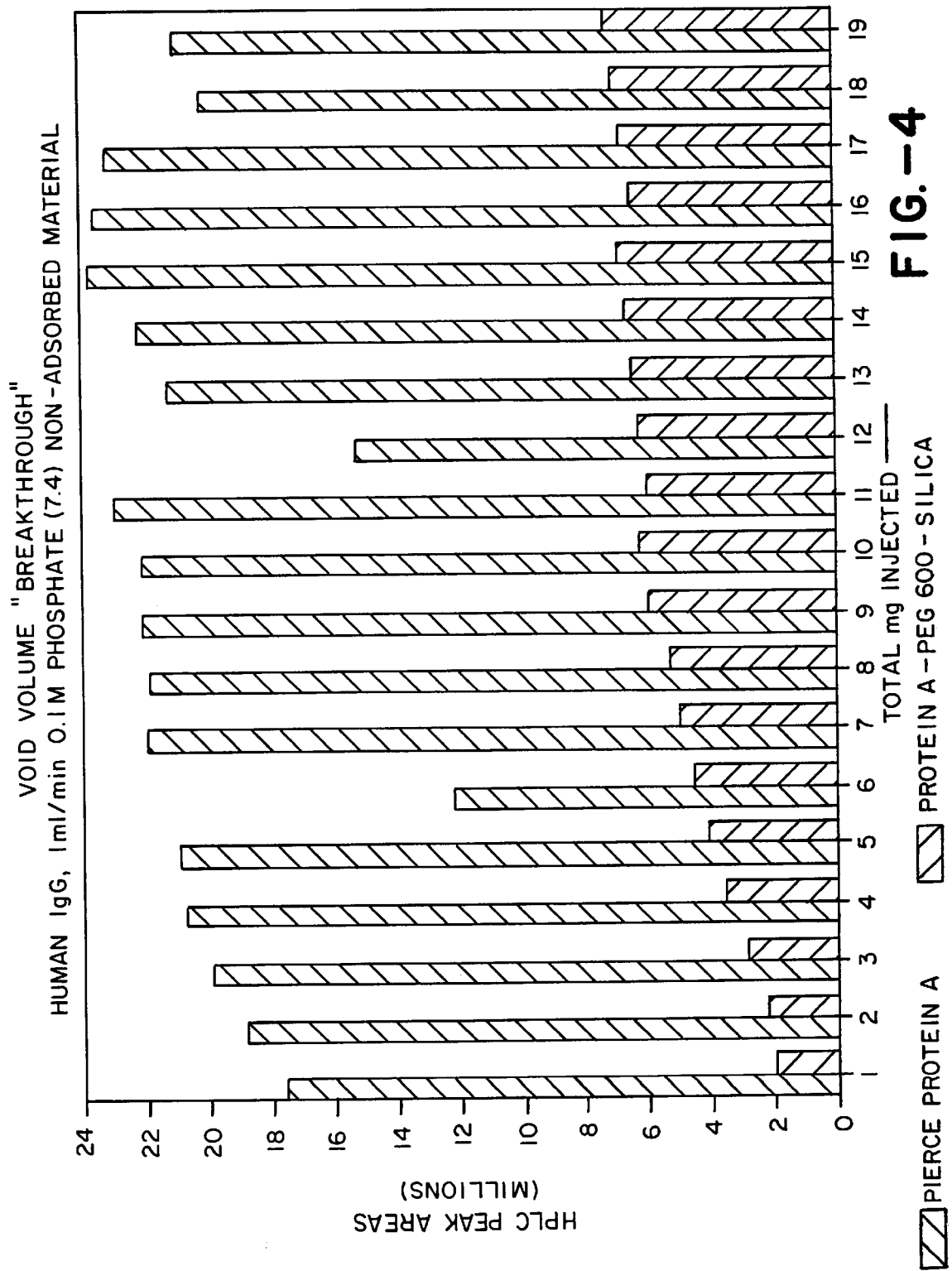
FIG. 4 depicts the binding of human IgG to Protein A bound to silica via a 7-atom linker and to silica via a 45 atom PEG molecule.

The effect of long spacer molecules was tested with Protein A-coupled via PEG 600 and compared to a Protein A column manufactured by Pierce Chemicals (Rockford, Ill.) wherein the Protein A is coupled via a 7-atom linker (3-glycidoxypropyl). The kinetics of binding human IgG were measured by injecting 1.0 mg portions of human IgG into the coumn and measuring the area of the eluted peak which "breaks through" the column in the void volume. The bar graph in FIG. 4 shows the integrated peak areas for the 7-atom linked Protein A column (Pierce) were greater than for the Protein A-PEG 600-silica column. The greater peak areas show that the rate of binding of the human IgG eluting through the column is greater when the Protein A is linked to silica by a PEG 600 molecule.

The data in the bar graph were treated by a kinetic analysis in order to derive the rate constant for the IgG and Protein A binding reaction:

$$Af + Sf \rightarrow SA$$

Sf=free binding sites (mg/g of gel)
Af=free analyte molecule (mg/col volume)

$$\frac{d[Af]}{dt} = k[Af] = ([Sf] - [SA])$$

St=total binding sites (mg/g of gel)
SA=amount of bound analyte
t=reaction time (residence time in column)

$$ln\ [Af] = kt[St] - kt[SA]$$

By plotting (ln Af) vs [SA], and analyzing by linear regression, the factors k and St are:

$$k = slope/t$$

$$St = y\ intercept/slope$$

Figure 5:
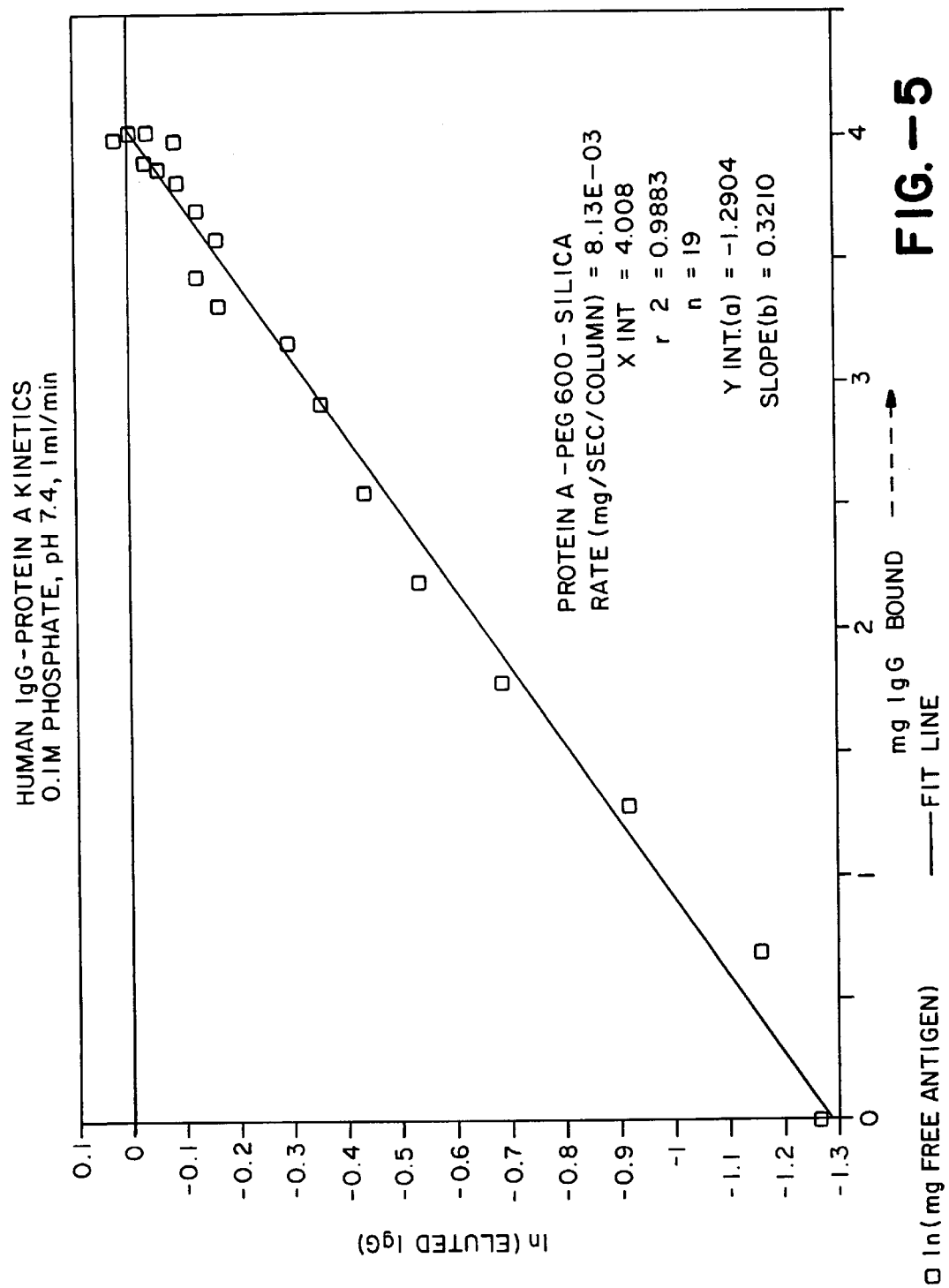
FIGS. 5 and 6 show a semi-log kinetic plot for human IgG binding to Protein A linked to silica via a 7-atom linker and a 45 atom PEG spacer.
Figure 6:
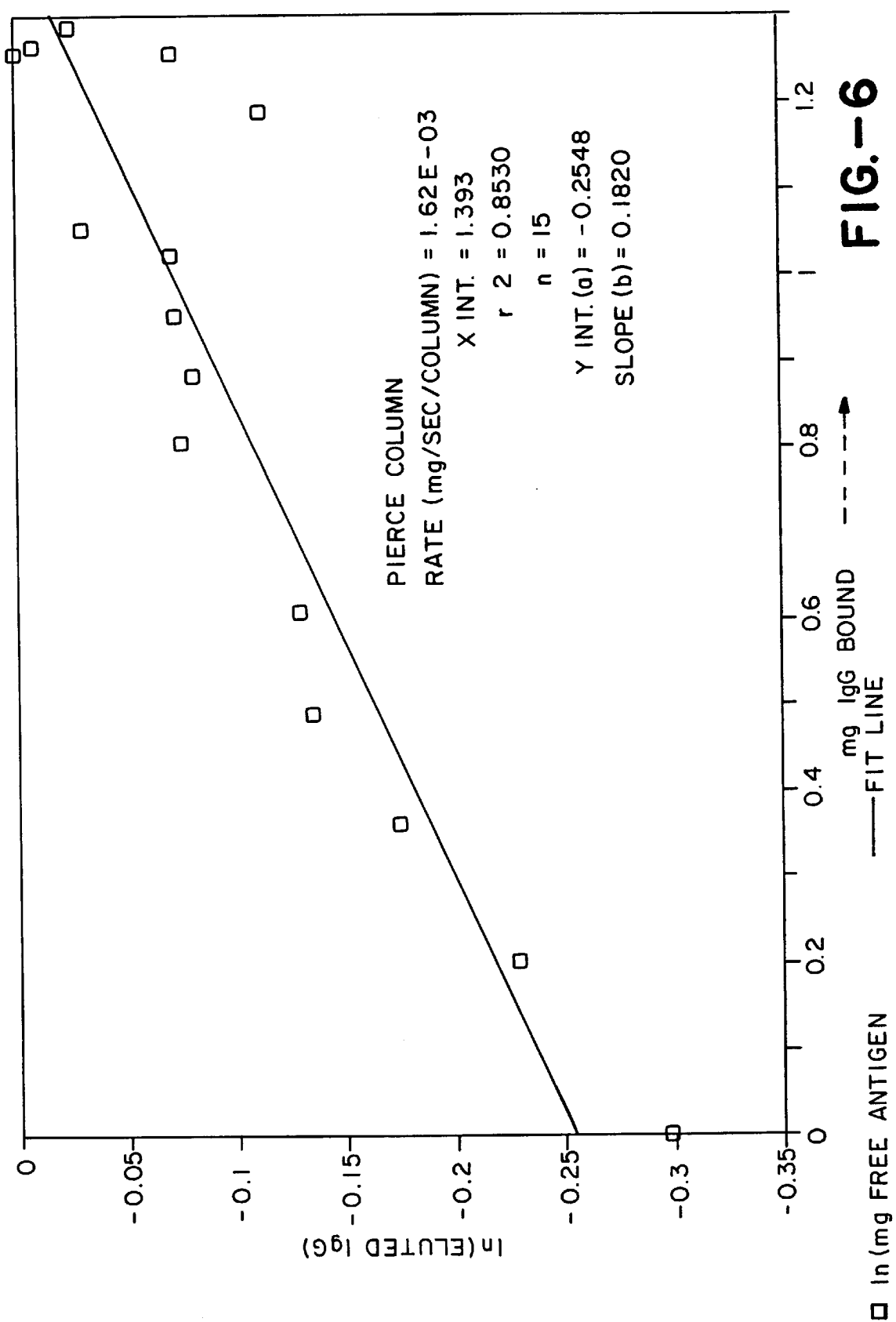

FIGS. 5 and 6 show the comparable plots for the Protein A-PEG 600-silica column and the 7-atom linked Protein A column respectively. The slope for the former was 0.32 and the slope for the latter was 0.18 when the columns were eluted at 1 ml/min.

The importance of the effect of at the almost two-fold increase in binding kinetics is graphically illustrated in the bar graph of FIG. 4. The 7-atom linked Protein A column is severly limited in its capability to purify IgG at the kind of speeds necessary for industrial utilization.

EXAMPLE 20

PBA Affinity Chromatography Experiments

The phenyl boronic acid (PBA)-PEG 600-silica prepared by the method of Example 8 was packed in an HPLC column and evaluated for its ability to retain molecules which possess 1,2-cis -diol or 1,2-cis -amino alcohol functional groups. Previously cis-diols were analyzed using PBA coupled to silica by-glycidoxypropyl silane (Glad, M., et al., *J. Chromatography* (1980), 254–260) or PBA coupled to cellulose (Moore, E. C., et al., *Biochemistry*, 13 (1974), 2904–07).

The test molecules containing diol or cis-amino alcohol functional groups were tested for adsorption on the HPAC column containing PBA-PEG 600 silica. This coulmn was eluted with either acetonitrile or sodium phosphate buffer (pH 7.5). If the compound was bound to the phenyl boronic acid and did not elute from the column, the mobile phase was changed to pH 4 (1% acetic acid) to elute the compound. The following table summarizes the behavior of the molecules tested on the PBA-PEG 600-silica.

| AFFINITY CHROMATOGRAPHY EXPERIMENTS WITH P600-PBA PRODUCT | | | |
|---|---|---|---|
| Molecule | Acetonitrile | pH 7.5 Buffer | pH <4 |
| Thymidine glycol | --------- | -------------- | --------- |
| Thymine glycol | --------- | -------------- | --------- |
| Uracil | --------- | -------------- | --------- |
| Adenosine | --------- | -------------- | --------- |
| Deoxythymidine | --------- | -------------- | --------- |
| Glycosylated hemoglobin | ND | slightly | --------- |
| Seratonin | +++++++++ | ++++++++++++++ | --------- |
| Epinephrine | +++++++++ | ++++++++++++++ | --------- |
| Norepinephrine | +++++++++ | ++++++++++++++ | --------- |
| Doxorubicin | +++++++++ | ++++++++++++++ | --------- |
| Daunorubicin | +++++++++ | ++++++++++++++ | --------- |
| Human serum | ND | -------------- | --------- |
| Bovine serum albumin | ND | -------------- | --------- |

ND = not done
+++++++++ = retained
--------- = eluted

The failure of thymidine glycol, thymine glycol, uracil, adenosine and glycosylated hemoglobin to bind to the column was unexpected.

EXAMPLE 21

Use of Napthoyl-PEG 600-Silica for Affinity Isolation of 5'-Dimethoxytritylated Synthetic Deoxyribonucleotides Gene synthesizer machines, which are having a major impact in development of medical research, produce (DNA) gene sequences which are contaminated by undesired shorter sequences resulting from the less than quantitative yield from the coupling steps in the synthesis. Purification of 5'-DMT protected sequences from shorter undesired DNA sequences has previously been achieved by affinity chromatography on napthoylated-celluose (Cashion, P. J., et al. (1973), *Biochem.* 12, 1985–1990). Such separations, however, are slow, sometimes taking more than ten hours to complete.

Figure 7:
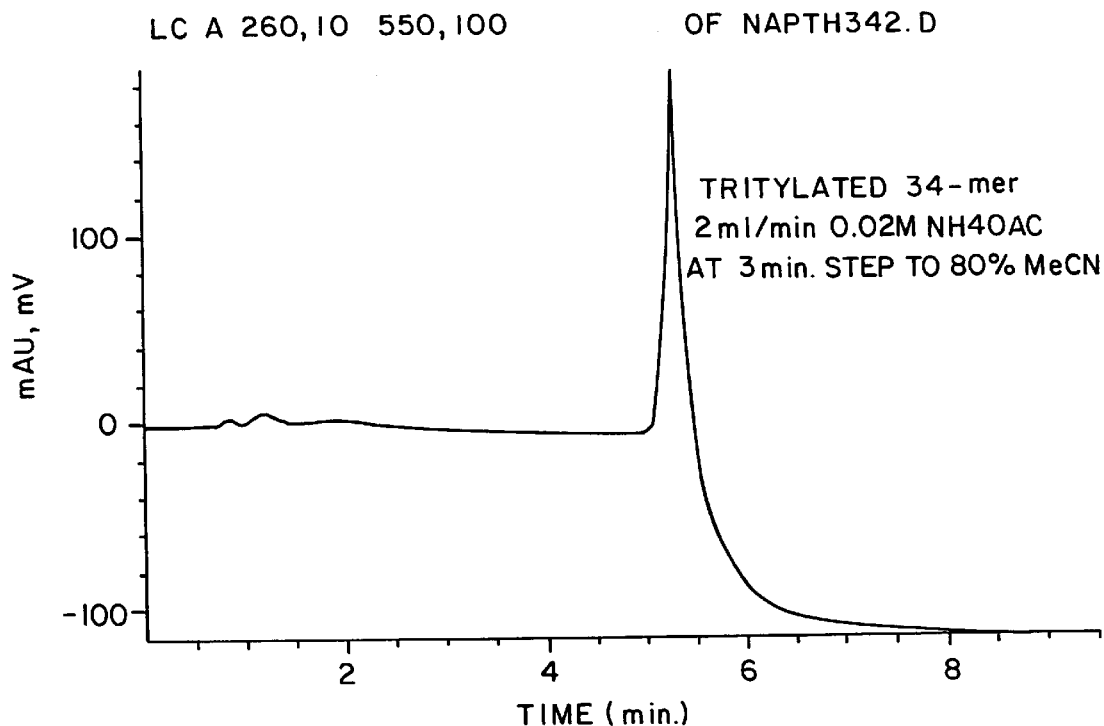
FIGS. 7 and 8 are chromatograms depicting the isolation of a 5' dimethoxytritylated 34-mer single stranded DNA sequence and a nonprotected 34-mer single stranded DNA sequence.
Figure 8:
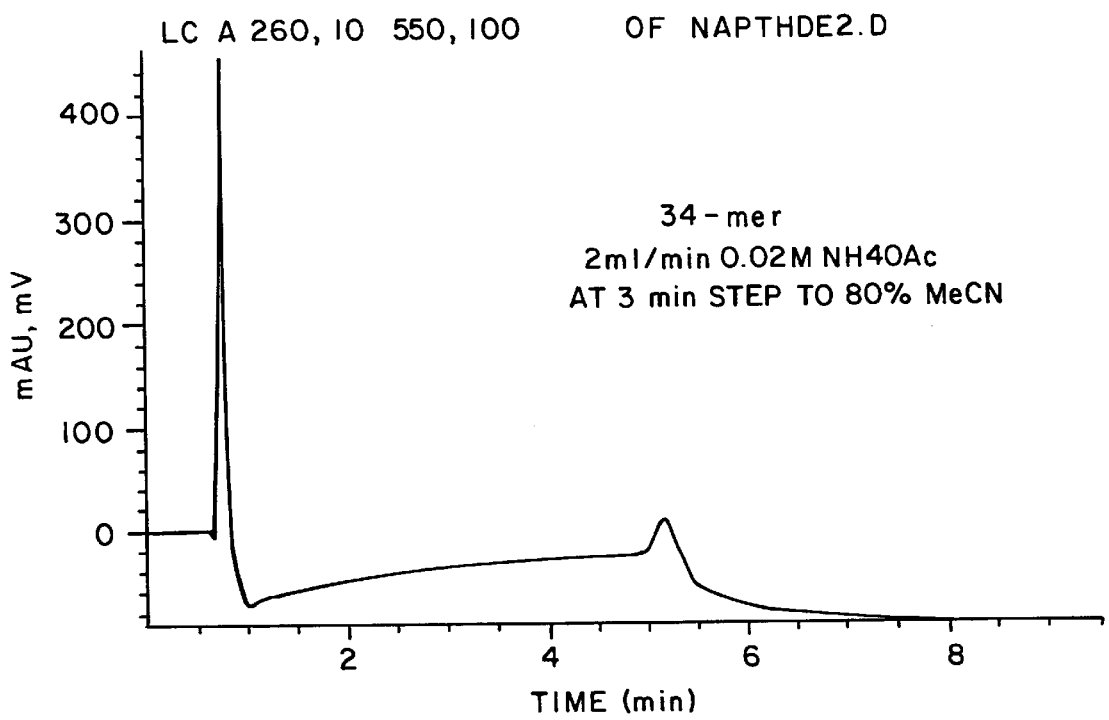

Chromatograms showing the chromatographic isolation of a 5'-dimethoxytritylated 34-mer and the isolation of a deprotected 34-mer DNA sequence are shown in FIGS. 7 and 8. The chromatographic material used in this experiment was the napthoyl-PEG 600-silica prepared by the method of Example 6. These results, while qualitatively similar to those obtained with napthoylated-cellulose, were obtained using linear flow rates which permitted the entire chromatogram to be developed in a matter of minutes rather than the hours required when using napthoylated-cellulose.

EXAMPLE 22

PEG 600-Sulfonated Polystyrene

Sulfonated cross-linked polystyrene is converted into the sulfonyl chloride by treatment with two equivalents of thionyl chloride in pyridine at 0° C. for two hours. The solvent is then decanted and the sulfonyl chloride-polystyrene is washed two times with dioxane. Ethylene diamine (1:10 v/v in dioxane) is then added in a 10 molar excess to the sulfonyl chloride resin to convert it into a sulfonamide linked primary amine resin.

To couple the PEG 600 to the amine derivatized resin, four equivalents of PEG 600 are activated by two moles of carbonyldiimidazole/mole PEG by stirring in dry dioxane at 35° C. for 30 minutes. This dioxane solution is then added to the amine derivatized polystyrene to afford a urethane linked PEG with a carbonyl-diimidazole activated terminus (PEG 600-polystyrene).

EXAMPLE 23

Immunoassay on PEG-Polystyrene

The CDI activated polystyrene is exposed to 1.0 mg of goat anti-human IgG (Sigma) in 4.0 ml of 0.1M sodium phosphate buffer (pH 7.4). Unreacted antibody is removed by rinsing three times with the same buffer to afford a polystyrene surface to which the human IgG is linked via PEG. Unreacted CDI groups are quenched by treatment with 4 ml of glucoseamine at 5 mg/ml for 30 minutes at ambient temperature.

The anti-human IgG-PEG 600-polystyrene surface is then exposed to 1 nanogram/ml of human IgG (Sigma) in phosphate buffer for five minutes. The surface is then rinsed three times with buffer. Anti-human IgG (0.25 ml, diluted to 1 ml Sigma) alkaline phosphatase conjugate is then exposed to the surface for five minutes. Unreacted anti-human IgG alkaline phosphatase conjugate is removed by rinsing three times with buffer. A 4 ml solution of 10 mmol/1 paranitrophenyl phosphate (Sigma) is then exposed to the surface. After five minutes, a blue color develops indicating presence of the human IgG. A negative control experiment is performed by using bovine serum albumin in place of the human IgG.

The amount of human IgG in an unknown sample is determined by preparing a standard spectrophotometric calibration curve for a range of human IgG concentrations. Thereafter, the sample containing an unknown amount of human IgG is serially diluted and assayed as described to quantify the amount of human IgG present in the original sample.

EXAMPLE 24

Purification of Rabbit Anti-Ovalbumin IgG's on the Ovalbumin Silica

Figure 9:
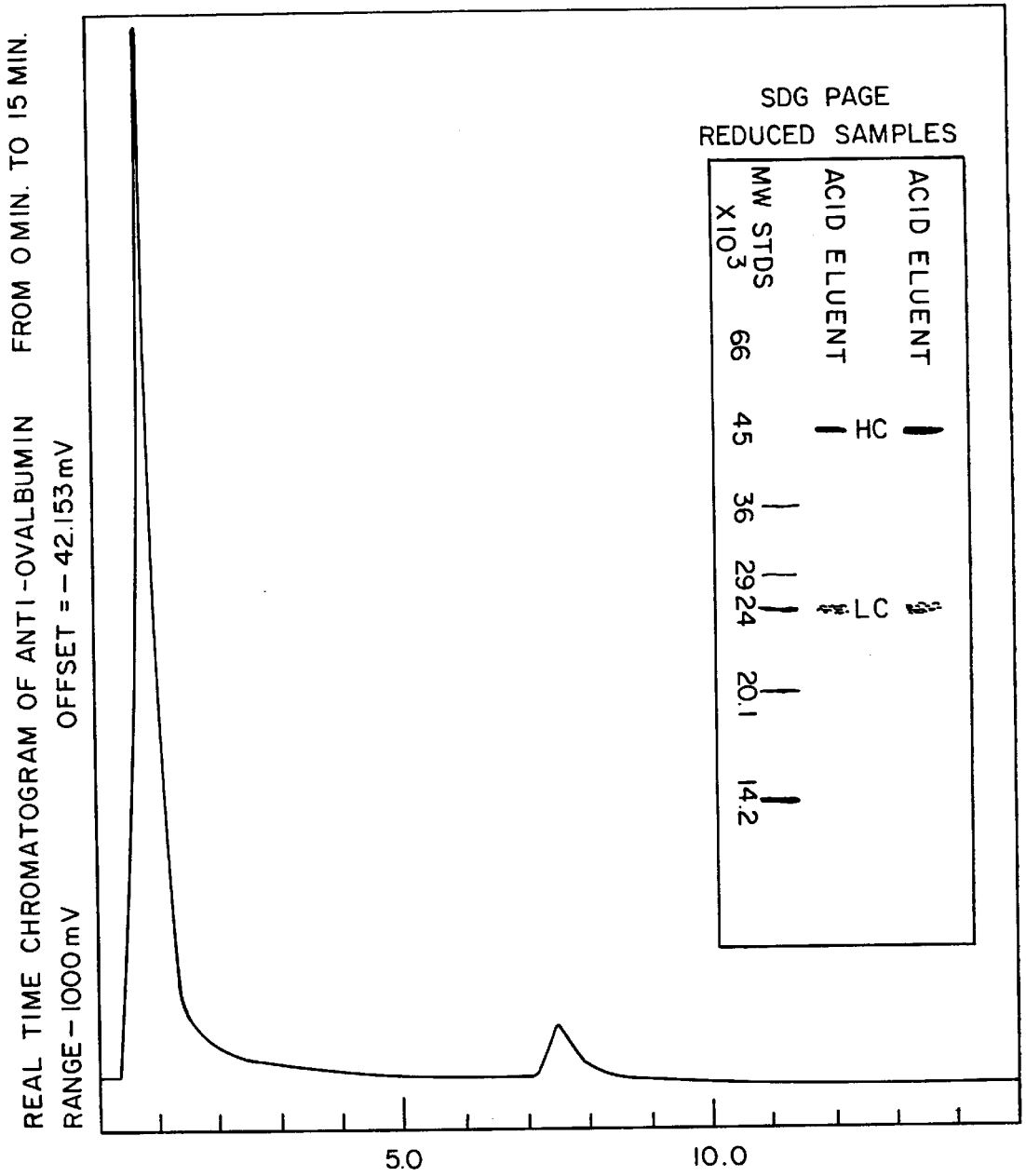
FIG. 9 is a chromatogram depicting the purification of rabbit anti-albumin IgG on ovalbumin silica. In addition, FIG. 9 contains an insert showing the electrophoretic mobility of the acid eluent obtained from the ovalbumin silica column.

Serum from a rabbit immunized against ovalbumin was loaded onto a column (10×0.46 cm) packed with the ovalbumin silica of Example 12. Nonbound serum components were removed by washing with 0.01M Na phosphate buffer, pH 7.4, containing 0.15 M NaCl. IgG was eluted with 2% acetic acid containing 0.15 M NaCl. A chromatogram of this experiment is shown n FIG. 9. Identity of the eluent was confirmed by sodium dodecyl sulfate-polyacrylamide gel electrophoresis and by Western blot analysis of antigen-binding activity. Coomassie blue stained gels of the reduced acid eluate show major bands with the same Rf values as the heavy and light chains IgG (FIG. 9, insert). Western blots on lanes containing chick embryo extract binding shows binding of the acid eluate only to ovalbumin.

EXAMPLE 25

Human IgG Adsorbing Capacity of Protein G Silica

Human IgG (60 mg, gamma globulin, Sigma) was dissolved in 12 ml of 0.01 M Na phosphate buffer, pH 7.4, containing 0.15 M NaCl. The solution was pumped at 1.0 ml/min. through a column (10×0.46 cm) packed with the Protein G silica of Example 14. The column was then washed with 80 ml of the same buffer to remove nonbound IgG from the column. The IgG was desorbed by pumping 10 ml of 2% acetic acid with 0.15 M NaCl through the column and the acid eluent was collected. The amount of IgG (36 mg) in the acid eluent was quantified by OD 280 nm ansorbance and comparison with a calibration line of OD 280 nm versus IgG concentration in 2% acetic acid with 0.15 M NaCl.

EXAMPLE 26

Purification of IgG from Mouse Serum on Protein G Silica

Figure 10:
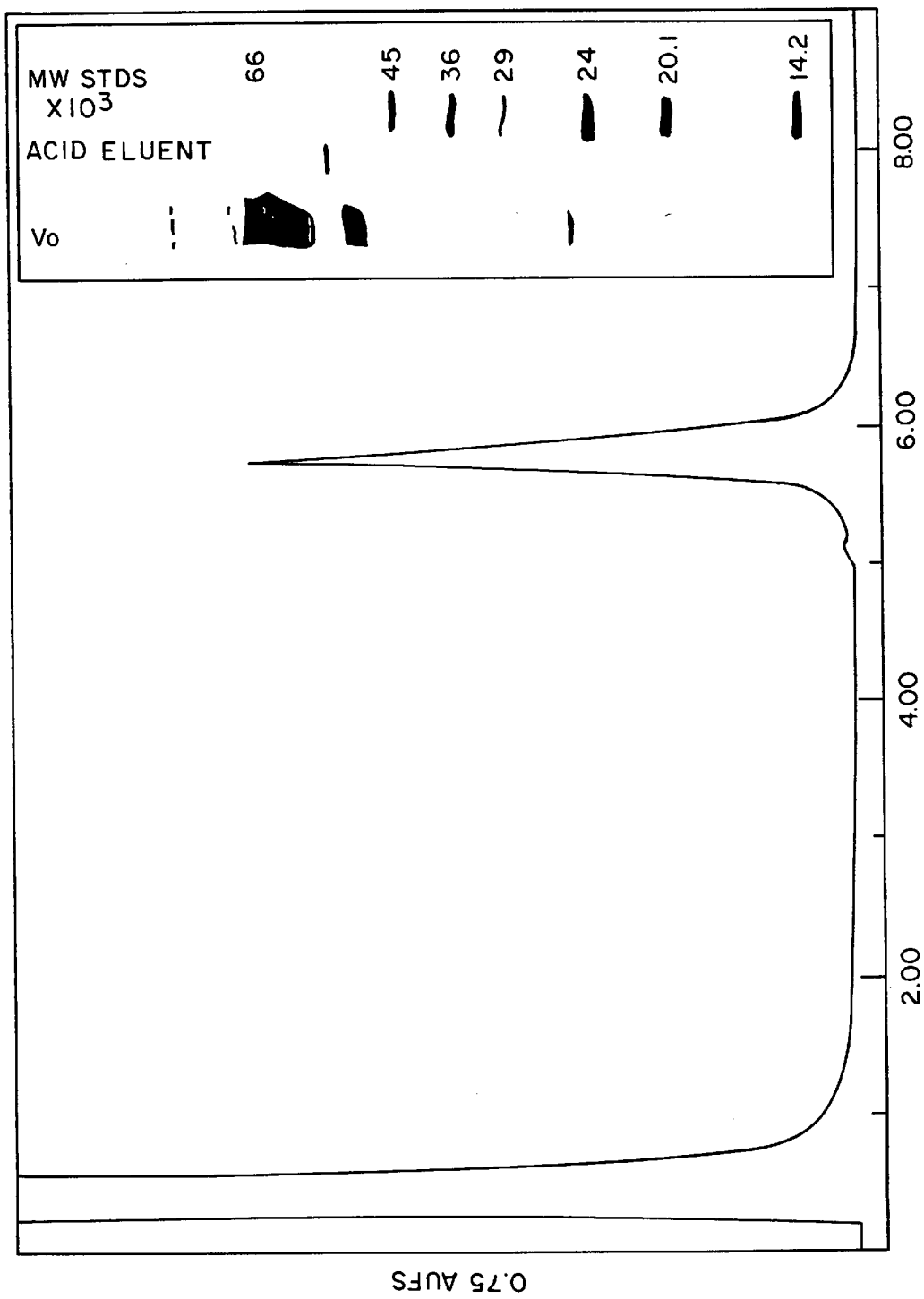
FIG. 10 is a chromatogram depicting the separation of IgG from mouse serum on protein G silica. In addition, the electrophratic mobility of the acid eluent is depicted by the insert to FIG. 10.

Normal mouse serum (200 µl) was injected onto a Protein G silica column (10×0.46 cm) at 4.0 ml/min. flow rate. The column was washed with 0.01 M Na phosphate buffer, pH 7.4, containing 0.15 M NaCl to remove nonbound serum components. The IgG was eluted with 2% acetic acid containing 0.15 M NaCl. A chromatogram of this experiment is shown in FIG. 10. Identity of the acid eluted peak was confirmed by sodium dodecyl sulfate-polyacrylamide gel electrophoresis (FIG. 10 insert.)

EXAMPLE 27

Purification of IgG from Hybridoma Supernatants on Protein G Silica

Supernatant from hybridoma culture (10 ml) was loaded onto the Protein G silica column (10×0.46 cm) at 2.0 ml/min. flow rate. The column was washed with 0.01 M Na phosphate buffer, pH 7.4, containng 0.15 M NaCl to remove nonbound serum components. The IgG was eluted with 2% acetic acid containing 0.15 M NaCl. A chromatogram of this experiment is shown in FIG. 11.

Identity of the acid eluted peak was confirmed by sodium dodecyl sulfate-polyacrylamide gel electrophoresis (FIG. 11 insert.)

EXAMPLE 28

Isolation of BSA on Anti-BSA Column

Figure 13:
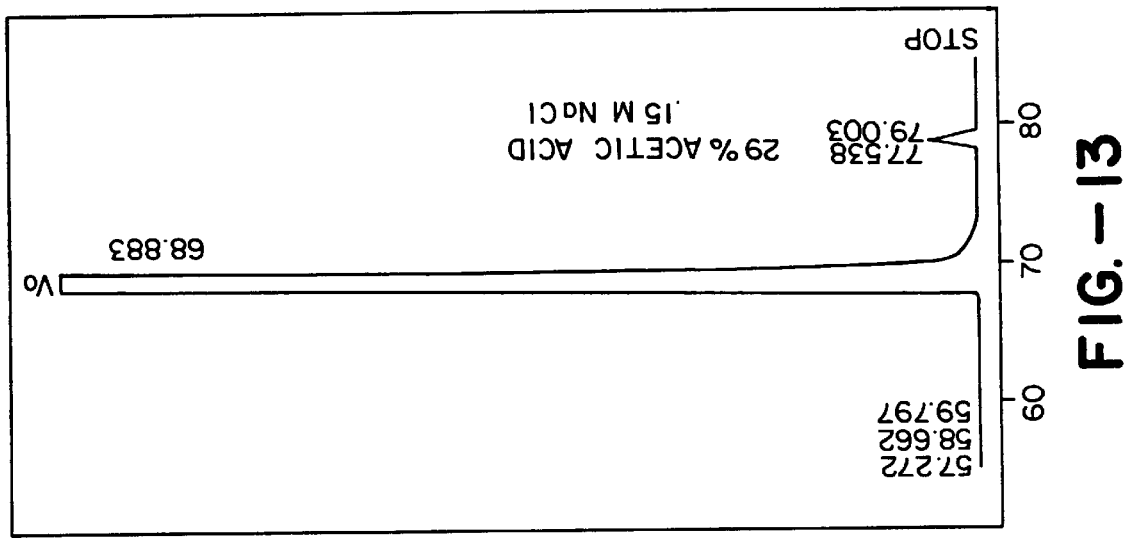
FIG. 13 is a chromatogram depicting the purification of bovine serum albumin from fetal bovine serum.
Figure 12:
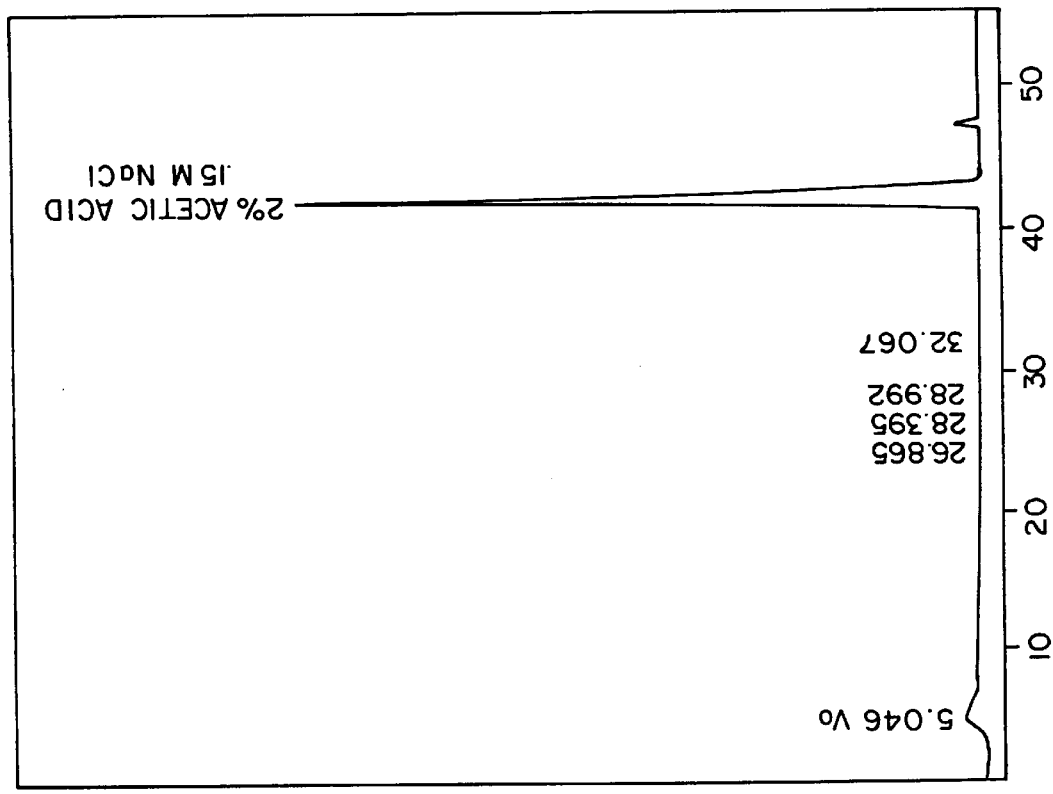
FIG. 12 is a chromatogram depicting the isolation of bovine serum albumin on an anti-BSA silica column.

BSA at 5 mg/ml in 0.01 M Na phosphate, 0.15 M NaCl, pH 7.4, was injected in the anti-BSA column. At a flow rate of 50 µl of BSA was injected. The column was washed and BSA was eluted with 2% HOAc, 0.15 M NaCl at 2 ml/min. followed by 20% HOAc, 0.15 M NaCl at 2 ml/min. (FIG. 12). At a flow rate of 1 ml/min., 500 µl of fetal bovine serum was injected, the column was washed and BSA was eluted with 2% HOAc, 0.15 M NaCl at 2 mo/min. (FIG. 13). Isolation of BSA on the anti-BSA column was confirmed by gel electrophoresis on the 2% elution samples.

Having described the preferred embodiments of the present invention, it will appear to those ordinarily skilled in the art that various modifications may be made to the disclosed embodiments, and that such modifications are intended to be within the scope of the present invention.

What is claimed is:

1. A process for the separation of at least one substance from a mixture comprising the steps of:
   (a) contacting a mixture containing the at least one substance with an affinity ligand retained on a composition to bind said substance to said affinity ligand, said composition having the formula S-B-X-Y-L wherein S is a substantially non-compressible solid support comprising silica, B is a binding group containing silicon covalently linked to a silanol group of S through a siloxane bond, X is a substantially non-ionic hydrophilic spacer comprising polyethylene glycol having between 4 and 300 ethylene glycol units, Y is a coupling group and L is said affinity ligand, and (b) passing an eluting solution through the chromatographic material to recover the at least one substance from said composition, wherein the adsorption rate constant for said binding is greater than that for the same process using a composition having the formula S-B-L, and wherein said process is performed at a pressure greater than 500 psi and a linear flow velocity greater than approximately 0.1 cm/min.

2. A process for the separation and detection of at least one substance in a mixture comprising the steps of:

(a) contacting a mixture containing the at least one substance with the affinity ligand retained on a composition to bind said substance to said affinity ligand, said composition having the formula S-B-X-Y-L wherein S is a substantially non-compressible solid support comprising silica, B is a binding group containing silicon covalently linked to a silanol group of S through a siloxane bond, X is a substantially non-ionic hydrophilic spacer comprising polyethylene glycol having between 4 and 300 ethylene glycol units, Y is a coupling group and L is said affinity ligand, and (b) determining the presence of said one substance bound to said composition, wherein the adsorption rate constant for said binding is greater than that for the same process using a composition having the formula S-B-L, and wherein said process is performed at a pressure greater than 500 psi and a linear flow velocity greater than approximately 0.1 cm/min.

3. A process for the separation of at least one substance from a mixture comprising the steps of:

(a) contacting a fluid containing said mixture with a composition to bind said substance to an affinity ligand, said composition having the formula S-B-X-Y-L wherein S is a substantially non-compressible solid support comprising silica, B is a binding group containing silicon covalently linked to a silanol group of S through a siloxane bond, X is a substantially non-ionic hydrophilic spacer comprising polyethylene glycol having between 4 and 300 ethylene glycol units, Y is a coupling group and L is said affinity ligand, and (b) separating said fluid from said composition with said at least one substance bound thereto wherein the adsorption rate constant for said binding is greater than that for the same process using a composition having the formula S-B-L, and wherein said process is performed at a pressure greater than 500 psi and a linear flow velocity greater than approximately 0.1 cm/min.

4. A process for the separation of at least one substance from a mixture comprising the steps of:

(a) contacting a mixture containing the at least one substance with an affinity ligand retained on a composition to bind said substance to said affinity ligand, said composition having the formula S-B-X-Y-L wherein S is a substantially non-compressible solid support comprising silica, B is a binding group containing silicon covalently linked to a silanol group of S through a siloxane bond, X is a substantially non-ionic hydrophilic spacer comprising polyethylene glycol having between 4 and 300 ethylene glycol units, Y is a coupling group and L is said affinity ligand, and (b) passing an eluting solution through the chromatographic material to recover the at least one substance from said composition, wherein the adsorption rate constant for said binding is greater than that for the same process using a composition having the formula S-B-L, and wherein said process is performed at a pH level above 8.5.

5. A process for the separation and detection of at least one substance in a mixture comprising the steps of:

(a) contacting a mixture containing the at least one substance with the affinity ligand retained on a composition to bind said substance to said affinity ligand, said composition having the formula S-B-X-Y-L wherein S is a substantially non-compressible solid support comprising silica, B is a binding group containing silicon covalently linked to a silanol group of S through a siloxane bond, X is a substantially non-ionic hydrophilic spacer comprising polyethylene glycol having between 4 and 300 ethylene glycol units, Y is a coupling group and L is said affinity ligand, and (b) determining the presence of said one substance bound to said composition, wherein the adsorption rate constant for said binding is greater than that for the same process using a composition having the formula S-B-L, and wherein said process is performed at a pH level above 8.5.

6. A process for the separation of at least one substance from a mixture comprising the steps of:

(a) contacting a fluid containing said mixture with a composition to bind said substance to an affinity ligand, said composition having the formula S-B-X-Y-L wherein S is a substantially non-compressible solid support comprising silica, B is a binding group containing silicon covalently linked to a silanol group of S through a siloxane bond, X is a substantially non-ionic hydrophilic spacer comprising polyethylene glycol having between 4 and 300 ethylene glycol units, Y is a coupling group and L is said affinity ligand, and (b) separating said fluid from said composition with said at least one substance bound thereto wherein the adsorption rate constant for said binding is greater than that for the same process using a composition having the formula S-B-L, and wherein said process is performed at a pH level above 8.5.

* * * * *